United States Patent
Eichmann et al.

(10) Patent No.: US 11,998,229 B2
(45) Date of Patent: Jun. 4, 2024

(54) ULTRASONIC DEVICE FOR CUTTING AND COAGULATING

(71) Applicant: Cilag GmbH International, Zug (CH)

(72) Inventors: Stephen E. Eichmann, Cincinnati, OH (US); Karen K. Isaacs, Edgewood, KY (US); Kenneth S. Kramer, Trabuco Canyon, CA (US); Michael R. Lamping, Cincinnati, OH (US); Ashvani K. Madan, Mason, OH (US); Matthew C. Miller, Cincinnati, OH (US); Aaron C. Voegele, Loveland, OH (US); Eitan T. Wiener, Cincinnati, OH (US); Joseph E. Young, Loveland, OH (US)

(73) Assignee: Cilag GmbH International, Zug (CH)

( * ) Notice: Subject to any disclaimer, the term of this patent is extended or adjusted under 35 U.S.C. 154(b) by 279 days.

(21) Appl. No.: 17/112,272

(22) Filed: Dec. 4, 2020

(65) Prior Publication Data
US 2021/0145473 A1    May 20, 2021

Related U.S. Application Data

(60) Continuation of application No. 15/690,925, filed on Aug. 30, 2017, now Pat. No. 10,856,896, which is a
(Continued)

(51) Int. Cl.
*A61B 17/32*     (2006.01)
*A61B 17/16*     (2006.01)
(Continued)

(52) U.S. Cl.
CPC .. *A61B 17/320092* (2013.01); *A61B 17/1606* (2013.01); *A61B 17/2841* (2013.01);
(Continued)

(58) Field of Classification Search
CPC ........ A61B 17/320092; A61B 17/1606; A61B 17/162; A61B 17/8875;
(Continued)

(56) References Cited

U.S. PATENT DOCUMENTS

| 969,528 A | 9/1910 | Disbrow |
|---|---|---|
| 1,570,025 A | 1/1926 | Young |

(Continued)

FOREIGN PATENT DOCUMENTS

| CA | 837241 A | 3/1970 |
|---|---|---|
| CA | 2535467 A1 | 4/1993 |

(Continued)

OTHER PUBLICATIONS

Technology Overview, printed from www.harmonicscalpel.com, Internet site, website accessed on Jun. 13, 2007, (3 pages).
(Continued)

*Primary Examiner* — Sarah A Long

(57) ABSTRACT

An ultrasonic surgical system is disclosed comprising a surgical instrument and a wrench assembly. The surgical instrument comprises a handle assembly and a body member pivotably coupled to the handle assembly. The handle assembly comprises a first finger grip, an ultrasonic blade, and a waveguide extending proximally from the ultrasonic blade. The body member comprises a second finger grip, a clamp arm movable relative to the ultrasonic blade to capture tissue therebetween, a first body surface defined on a first side of the body member, and a second body surface defined on a second side of the body member. The wrench assembly comprises a wrench and an adapter operably coupled to the wrench. The adapter comprises a first wrench surface configured to engage the first body surface and a second wrench surface configured to engage the second body surface.

20 Claims, 32 Drawing Sheets

Related U.S. Application Data continuation of application No. 14/223,121, filed on Mar. 24, 2014, now abandoned, which is a continuation of application No. 13/311,695, filed on Dec. 6, 2011, now abandoned, which is a division of application No. 11/548,407, filed on Oct. 11, 2006, now abandoned.

(60) Provisional application No. 60/726,625, filed on Oct. 14, 2005.

(51) Int. Cl.
  *A61B 17/28* (2006.01)
  *A61B 17/00* (2006.01)
  *A61B 17/88* (2006.01)

(52) U.S. Cl.
  CPC .......... *A61B 2017/00424* (2013.01); *A61B 2017/00477* (2013.01); *A61B 2017/00738* (2013.01); *A61B 17/162* (2013.01); *A61B 2017/2825* (2013.01); *A61B 2017/320075* (2017.08); *A61B 2017/320093* (2017.08); *A61B 2017/320094* (2017.08); *A61B 2017/320095* (2017.08); *A61B 17/8875* (2013.01)

(58) Field of Classification Search
  CPC .......... A61B 2017/00424; A61B 2017/00477; A61B 2017/00738; A61B 2017/320093; A61B 2017/320094; A61B 2017/320095
  See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,057,660 A | 11/1977 | Yoshida et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,169,984 A | 10/1979 | Parisi |
| 4,173,725 A | 11/1979 | Asai et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,352,459 A | 10/1982 | Berger et al. |
| 4,445,063 A | 4/1984 | Smith |
| 4,452,473 A | 6/1984 | Ruschke |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,696,667 A | 9/1987 | Masch |

(56) References Cited

U.S. PATENT DOCUMENTS

| | | | |
|---|---|---|---|
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,783,997 A | 11/1988 | Lynnworth |
| 4,808,154 A | 2/1989 | Freeman |
| 4,819,635 A | 4/1989 | Shapiro |
| 4,821,719 A | 4/1989 | Fogarty |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,861,332 A | 8/1989 | Parisi |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,978,067 A | 12/1990 | Berger et al. |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,057,119 A | 10/1991 | Clark et al. |
| 5,058,570 A | 10/1991 | Idemoto et al. |
| 5,059,210 A * | 10/1991 | Clark ............... A61B 17/3215 464/37 |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,613 A | 10/1992 | Sawyer |
| 5,156,633 A | 10/1992 | Smith |
| 5,159,226 A | 10/1992 | Montgomery |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,209,776 A | 5/1993 | Bass et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,385 A | 9/1993 | Strukel |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,289,436 A | 2/1994 | Terhune |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| 5,306,280 A | 4/1994 | Bregen et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,327 A | 5/1994 | Bales et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,297 A | 6/1994 | Hood et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,338,292 A | 8/1994 | Clement et al. |
| 5,339,723 A | 8/1994 | Huitema |
| 5,342,292 A | 8/1994 | Nita et al. |
| 5,342,359 A | 8/1994 | Rydell |
| 5,344,420 A | 9/1994 | Hilal et al. |
| 5,345,937 A | 9/1994 | Middleman et al. |

(56) References Cited

U.S. PATENT DOCUMENTS

| | | |
|---|---|---|
| 5,346,502 A | 9/1994 | Estabrook et al. |
| 5,353,474 A | 10/1994 | Good et al. |
| 5,354,265 A | 10/1994 | Mackool |
| 5,356,064 A | 10/1994 | Green et al. |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,372,585 A | 12/1994 | Tiefenbrun et al. |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,883 A | 1/1995 | Wilk et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,397,293 A | 3/1995 | Alliger et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| 5,409,453 A | 4/1995 | Lundquist et al. |
| D358,887 S | 5/1995 | Feinberg |
| 5,411,481 A | 5/1995 | Allen et al. |
| 5,413,107 A | 5/1995 | Oakley et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,496,411 A | 3/1996 | Candy |
| 5,499,992 A | 3/1996 | Meade et al. |
| 5,500,216 A | 3/1996 | Julian et al. |
| 5,501,654 A | 3/1996 | Failla et al. |
| 5,503,616 A | 4/1996 | Jones |
| 5,504,650 A | 4/1996 | Katsui et al. |
| 5,505,693 A | 4/1996 | Mackool |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,273 A | 6/1996 | Manna et al. |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,534 A | 11/1996 | Stone |
| 5,575,799 A | 11/1996 | Bolanos et al. |
| 5,577,654 A | 11/1996 | Bishop |
| 5,582,618 A | 12/1996 | Chin et al. |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,578 A | 5/1997 | Tihon |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,643,301 A | 7/1997 | Mollenauer |
| 5,647,851 A | 7/1997 | Pokras |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,709,680 A | 1/1998 | Yates et al. |
| 5,711,472 A | 1/1998 | Bryan |

(56) References Cited

U.S. PATENT DOCUMENTS

| | | |
|---|---|---|
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,725,536 A | 3/1998 | Oberlin et al. |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,735,875 A | 4/1998 | Bonutti et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,537 A | 8/1998 | Oberlin et al. |
| 5,797,941 A | 8/1998 | Schulze et al. |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,310 A | 9/1998 | Hood |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,810,869 A | 9/1998 | Kaplan et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,820,009 A | 10/1998 | Melling et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,290 A | 12/1998 | Winston |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,363 A | 3/1999 | Urich |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,893,880 A | 4/1999 | Egan et al. |
| 5,895,412 A | 4/1999 | Tucker |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,910,150 A | 6/1999 | Saadat |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,941,887 A | 8/1999 | Steen et al. |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,010,054 A | 1/2000 | Johnson et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,053,906 A | 4/2000 | Honda et al. |
| 6,056,735 A | 5/2000 | Okada et al. |
| 6,063,050 A | 5/2000 | Manna et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,544 A | 7/2000 | Hibner et al. |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |

(56) References Cited

U.S. PATENT DOCUMENTS

| | | |
|---|---|---|
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,217,591 B1 | 4/2001 | Egan et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,471 B1 | 8/2001 | Hechel et al. |
| 6,270,831 B2 | 8/2001 | Kumar et al. |
| 6,273,852 B1 | 8/2001 | Lehe et al. |
| 6,273,902 B1 | 8/2001 | Fogarty et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,293,954 B1 | 9/2001 | Fogarty et al. |
| 6,299,591 B1 | 10/2001 | Banko |
| 6,299,621 B1 | 10/2001 | Fogarty et al. |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,312,434 B1 | 11/2001 | Sutrina et al. |
| 6,312,445 B1 | 11/2001 | Fogarty et al. |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,333,488 B1 | 12/2001 | Lawrence et al. |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,387,112 B1 | 5/2002 | Fogarty et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,409,722 B1 | 6/2002 | Hoey et al. |
| 6,409,743 B1 | 6/2002 | Fenton, Jr. |
| H2037 H | 7/2002 | Yates et al. |
| 6,416,469 B1 | 7/2002 | Phung et al. |
| 6,416,486 B1 | 7/2002 | Wampler |
| 6,416,525 B1 | 7/2002 | Shibata |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,425,907 B1 * | 7/2002 | Shibata ........... A61B 17/320092 606/169 |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,286 B2 | 10/2002 | Mastri et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,498,421 B1 | 12/2002 | Oh et al. |
| 6,500,112 B1 | 12/2002 | Khouri |

(56) References Cited

U.S. PATENT DOCUMENTS

| | | |
|---|---|---|
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,526,976 B1 | 3/2003 | Baran |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B2 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,562,059 B2 | 5/2003 | Edwards et al. |
| 6,565,558 B1 | 5/2003 | Lindenmeier et al. |
| 6,569,109 B2 | 5/2003 | Sakurai et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,929 B2 | 6/2003 | Sussman et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,229 B2 | 8/2003 | Coss |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,444 B2 | 9/2003 | Babaev |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,839 B2 | 11/2003 | Manna et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,124 B2 | 12/2003 | Flesch et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,086 B1 | 2/2004 | Nita et al. |
| 6,689,145 B2 | 2/2004 | Lee et al. |
| 6,689,146 B1 | 2/2004 | Himes |
| 6,690,960 B2 | 2/2004 | Chen et al. |
| 6,692,514 B2 | 2/2004 | Fogarty et al. |
| 6,695,782 B2 | 2/2004 | Ranucci et al. |
| 6,695,840 B2 | 2/2004 | Schulze |
| 6,699,214 B2 | 3/2004 | Gellman |
| 6,702,761 B1 | 3/2004 | Damadian et al. |
| 6,702,821 B2 | 3/2004 | Bonutti |
| 6,712,805 B2 | 3/2004 | Weimann |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |

(56) References Cited

U.S. PATENT DOCUMENTS

| | | |
|---|---|---|
| 6,828,712 B2 | 12/2004 | Battaglin et al. |
| 6,832,988 B2 | 12/2004 | Sproul |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,221 B1 | 5/2005 | Baillargeon et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,466 B1 | 6/2005 | Bonutti et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,932,876 B1 | 8/2005 | Statnikov |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,989,017 B2 | 1/2006 | Howell et al. |
| 6,994,708 B2 | 2/2006 | Manzo |
| 6,994,709 B2 | 2/2006 | Lida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,354 B2 | 3/2006 | Tazi |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,062,314 B2 | 6/2006 | Zhu et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,036 B1 | 7/2006 | Adams |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,131,983 B2 | 11/2006 | Murakami |
| 7,135,018 B2 | 11/2006 | Ryan et al. |
| 7,135,029 B2 | 11/2006 | Makin et al. |
| 7,135,030 B2 | 11/2006 | Schwemberger et al. |
| 7,137,963 B2 | 11/2006 | Nita et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,182,762 B2 | 2/2007 | Bortkiewicz |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |

(56) References Cited

U.S. PATENT DOCUMENTS

| | | |
|---|---|---|
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,338,463 B2 | 3/2008 | Vigil |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,533,830 B1 | 5/2009 | Rose |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,627,936 B2 | 12/2009 | Bromfield |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |

(56) References Cited

U.S. PATENT DOCUMENTS

| | | |
|---|---|---|
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,763 B2 | 3/2010 | Vaezy et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,670 B2 | 4/2010 | Sakamoto |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,785,324 B2 | 8/2010 | Eberl |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,815,658 B2 | 10/2010 | Murakami |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter et al. |
| 7,834,484 B2 | 11/2010 | Sartor |
| 7,834,521 B2 | 11/2010 | Habu et al. |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,465 B2 | 2/2011 | Donofrio et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Likura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,716 B2 | 4/2011 | Malecki et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,006,358 B2 | 8/2011 | Cooke et al. |

(56) References Cited

U.S. PATENT DOCUMENTS

| | | |
|---|---|---|
| 8,016,843 B2 | 9/2011 | Escaf |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,011 B2 | 11/2011 | Okabe |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,137,263 B2 | 3/2012 | Marescaux et al. |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | Mckenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,353,847 B2 | 1/2013 | Kuhns et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,096 B2 | 3/2013 | Moses et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |

(56) References Cited

U.S. PATENT DOCUMENTS

| | | |
|---|---|---|
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,435,258 B2 | 5/2013 | Young et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,610,334 B2 | 12/2013 | Bromfield |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,691,268 B2 | 4/2014 | Weimann |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |

(56) References Cited

U.S. PATENT DOCUMENTS

| | | |
|---|---|---|
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,023,072 B2 | 5/2015 | Young et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |

(56) References Cited

U.S. PATENT DOCUMENTS

| | | |
|---|---|---|
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |

(56) References Cited

U.S. PATENT DOCUMENTS

| | | |
|---|---|---|
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,561,436 B2 | 2/2020 | Asher et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,603,064 B2 | 3/2020 | Zhang |
| 10,610,286 B2 | 4/2020 | Wiener et al. |
| 10,624,665 B2 | 4/2020 | Noui et al. |
| 10,624,691 B2 | 4/2020 | Wiener et al. |
| 10,639,092 B2 | 5/2020 | Corbett et al. |
| 10,646,267 B2 | 5/2020 | Ding |
| 10,677,764 B2 | 6/2020 | Ross et al. |
| 10,687,884 B2 | 6/2020 | Wiener et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,261 B2 | 7/2020 | Houser et al. |
| 10,729,458 B2 | 8/2020 | Stoddard et al. |
| 10,736,649 B2 | 8/2020 | Messerly et al. |
| 10,736,685 B2 | 8/2020 | Wiener et al. |
| 10,751,108 B2 | 8/2020 | Yates et al. |
| 10,758,294 B2 | 9/2020 | Jones |
| 10,779,845 B2 | 9/2020 | Timm et al. |
| 10,779,847 B2 | 9/2020 | Messerly et al. |
| 10,779,848 B2 | 9/2020 | Houser |
| 10,779,849 B2 | 9/2020 | Shelton, IV et al. |
| 10,779,879 B2 | 9/2020 | Yates et al. |
| 10,820,920 B2 | 11/2020 | Scoggins et al. |
| 10,820,938 B2 | 11/2020 | Fischer et al. |
| 10,828,056 B2 | 11/2020 | Messerly et al. |
| 10,828,057 B2 | 11/2020 | Neurohr et al. |
| 10,828,058 B2 | 11/2020 | Shelton, IV et al. |
| 10,828,059 B2 | 11/2020 | Price et al. |
| 10,835,307 B2 | 11/2020 | Shelton, IV et al. |
| 10,835,768 B2 | 11/2020 | Robertson et al. |
| 10,842,522 B2 | 11/2020 | Messerly et al. |
| 10,842,523 B2 | 11/2020 | Shelton, IV et al. |
| 10,842,580 B2 | 11/2020 | Gee et al. |
| 10,856,896 B2 | 12/2020 | Eichmann et al. |
| 10,874,418 B2 | 12/2020 | Houser et al. |
| 10,881,449 B2 | 1/2021 | Boudreaux et al. |
| 10,881,451 B2 | 1/2021 | Worrell et al. |
| 10,888,347 B2 | 1/2021 | Witt et al. |
| 10,893,883 B2 | 1/2021 | Dannaher |
| 10,912,603 B2 | 2/2021 | Boudreaux et al. |
| 10,952,759 B2 | 3/2021 | Messerly et al. |

(56) References Cited

U.S. PATENT DOCUMENTS

| | | |
|---|---|---|
| 10,959,769 B2 | 3/2021 | Mumaw et al. |
| 10,966,744 B2 | 4/2021 | Rhee et al. |
| 10,987,123 B2 | 4/2021 | Weir et al. |
| 11,000,707 B2 | 5/2021 | Voegele et al. |
| 11,006,971 B2 | 5/2021 | Faller et al. |
| 11,020,140 B2 | 6/2021 | Gee et al. |
| 11,033,292 B2 | 6/2021 | Green et al. |
| 11,033,322 B2 | 6/2021 | Wiener et al. |
| D924,400 S | 7/2021 | Kimball |
| 11,051,840 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,129,670 B2 | 9/2021 | Shelton, IV et al. |
| 11,134,978 B2 | 10/2021 | Shelton, IV et al. |
| 11,141,213 B2 | 10/2021 | Yates et al. |
| 11,179,582 B2 | 11/2021 | Voegele et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,253,288 B2 | 2/2022 | Robertson |
| 11,266,433 B2 | 3/2022 | Robertson |
| 11,272,952 B2 | 3/2022 | Messerly et al. |
| 11,324,527 B2 | 5/2022 | Aldridge et al. |
| 11,350,959 B2 | 6/2022 | Messerly et al. |
| 11,690,643 B2 | 7/2023 | Witt et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0032002 A1 | 10/2001 | McClurken et al. |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029054 A1 | 3/2002 | Rabiner et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0099373 A1 | 7/2002 | Schulze et al. |
| 2002/0107446 A1 | 8/2002 | Rabiner et al. |
| 2002/0107517 A1 | 8/2002 | Witt et al. |
| 2002/0120266 A1 | 8/2002 | Truckai et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0120306 A1 | 6/2003 | Burbank et al. |
| 2003/0130675 A1 | 7/2003 | Kasahara et al. |
| 2003/0130693 A1 | 7/2003 | Levin et al. |
| 2003/0139741 A1 | 7/2003 | Goble et al. |
| 2003/0144652 A1 | 7/2003 | Baker et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0195496 A1 | 10/2003 | Maguire et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212391 A1 | 11/2003 | Fenton et al. |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0049546 A1* | 3/2005 | Messerly ....... A61B 17/320092<br>606/169 |
| 2005/0070800 A1 | 3/2005 | Takahashi |
| 2005/0085728 A1 | 4/2005 | Fukuda |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0228425 A1 | 10/2005 | Boukhny et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0025802 A1 | 2/2006 | Sowers |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |

(56) References Cited

U.S. PATENT DOCUMENTS

| | | |
|---|---|---|
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1* | 4/2006 | Faller ............ A61B 17/320092 606/40 |
| 2006/0095046 A1 | 5/2006 | Trieu et al. |
| 2006/0100652 A1 | 5/2006 | Beaupre |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0241580 A1 | 10/2006 | Mittelstein et al. |
| 2006/0247558 A1 | 11/2006 | Yamada |
| 2006/0253050 A1 | 11/2006 | Yoshimine et al. |
| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0198005 A1 | 8/2007 | Ichihashi et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0276419 A1 | 11/2007 | Rosenthal |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0294051 A1 | 11/2008 | Koshigoe et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |

(56) References Cited

U.S. PATENT DOCUMENTS

| | | |
|---|---|---|
| 2010/0222752 A1 | 9/2010 | Collins, Jr. et al. |
| 2010/0228191 A1 | 9/2010 | Alvarez et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0078249 A1 | 3/2012 | Eichmann et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116363 A1 | 5/2012 | Houser et al. |
| 2012/0136279 A1 | 5/2012 | Tanaka et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2012/0330338 A1 | 12/2012 | Messerly |
| 2013/0023925 A1 | 1/2013 | Mueller |
| 2013/0072948 A1 | 3/2013 | States, III et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0197511 A1 | 8/2013 | Balanev et al. |
| 2013/0231691 A1 | 9/2013 | Houser |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2013/0331873 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0276963 A1 | 9/2014 | Ranucci et al. |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0083774 A1 | 3/2015 | Measamer et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0165240 A1 | 6/2015 | Stoddard et al. |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0114355 A1 | 4/2016 | Sakai et al. |
| 2016/0128769 A1 | 5/2016 | Rontal et al. |
| 2016/0175029 A1 | 6/2016 | Witt et al. |
| 2016/0206342 A1 | 7/2016 | Robertson et al. |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2017/0027624 A1 | 2/2017 | Wilson et al. |
| 2017/0036044 A1 | 2/2017 | Ito |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0202595 A1 | 7/2017 | Shelton, IV |
| 2017/0205234 A1 | 7/2017 | Honda |
| 2018/0125523 A1 | 5/2018 | Johnson |
| 2019/0053822 A1 | 2/2019 | Robertson et al. |
| 2019/0239919 A1 | 8/2019 | Witt et al. |
| 2019/0350615 A1 | 11/2019 | Messerly et al. |
| 2019/0380733 A1 | 12/2019 | Stulen et al. |
| 2020/0008857 A1 | 1/2020 | Conlon et al. |
| 2020/0015798 A1 | 1/2020 | Wiener et al. |
| 2020/0046401 A1 | 2/2020 | Witt et al. |
| 2020/0054386 A1 | 2/2020 | Houser et al. |
| 2020/0054899 A1 | 2/2020 | Wiener et al. |
| 2020/0085466 A1 | 3/2020 | Faller et al. |
| 2020/0323551 A1 | 10/2020 | Faller et al. |
| 2021/0038248 A1 | 2/2021 | Houser |
| 2021/0121197 A1 | 4/2021 | Houser et al. |
| 2021/0128191 A1 | 5/2021 | Messerly et al. |
| 2021/0145531 A1 | 5/2021 | Gee et al. |
| 2021/0236157 A1 | 8/2021 | Rhee et al. |
| 2021/0315605 A1 | 10/2021 | Gee et al. |
| 2021/0378700 A1 | 12/2021 | Houser |
| 2022/0257276 A1 | 8/2022 | Robertson |
| 2022/0346824 A1 | 11/2022 | Messerly et al. |
| 2023/0191161 A1 | 6/2023 | Wiener et al. |

FOREIGN PATENT DOCUMENTS

| | | |
|---|---|---|
| CA | 2214413 A1 | 9/1996 |
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 101766869 A | 7/2010 |
| CN | 202027624 U | 11/2011 |
| CN | 102335778 A | 2/2012 |
| CN | 103668171 A | 3/2014 |
| CN | 103921215 A | 7/2014 |
| CN | 106077718 A | 11/2016 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |

(56) References Cited

FOREIGN PATENT DOCUMENTS

| | | |
|---|---|---|
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1543854 A1 | 6/2005 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2454351 A1 | 11/1980 |
| FR | 2964554 A1 | 3/2012 |
| GB | 2032221 A | 4/1980 |
| GB | 2317566 A | 4/1998 |
| GB | 2318298 A | 4/1998 |
| GB | 2425480 A | 11/2006 |
| JP | S50100891 A | 8/1975 |
| JP | S5968513 U | 5/1984 |
| JP | S59141938 A | 8/1984 |
| JP | S62213746 A | 9/1987 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H04161078 A | 6/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H07185457 A | 7/1995 |
| JP | H07299415 A | 11/1995 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210296 A | 8/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2001057985 A | 3/2001 |
| JP | 2001170066 A | 6/2001 |
| JP | 2001198137 A | 7/2001 |
| JP | 2002035002 A | 2/2002 |
| JP | 2002186901 A | 7/2002 |
| JP | 2002233533 A | 8/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003230567 A | 8/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | 3841627 B2 | 11/2006 |
| JP | 2007177931 A | 7/2007 |
| JP | D1339835 S | 8/2008 |
| JP | 2009071439 A | 4/2009 |
| JP | 2009082904 A | 4/2009 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| JP | 2014121340 A | 7/2014 |
| JP | 2015529140 A | 10/2015 |
| JP | 2016022136 A | 2/2016 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9805437 A1 | 2/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0132087 A1 | 5/2001 |
| WO | WO-0167970 A1 | 9/2001 |
| WO | WO-0170112 A1 | 9/2001 |
| WO | WO-0195810 A2 | 12/2001 |
| WO | WO-02076685 A1 | 10/2002 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2008154338 A1 | 12/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

(56) References Cited

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).
Covidien Brochure, The LigaSure Precise™ Instrument, dated Mar. 2011 (2 pages).
AST Products, Inc., "Principles of Video Contact Angle Analysis," 20 pages, (2006).
Emam, Tarek A et al., "How Safe is High-Power Ultrasonic Dissection?," Annals of Surgery, (2003), pp. 186-191, vol. 237, No. 2, Lippincott Williams & Wilkins, Inc., Philadelphia, PA.
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.
Sadiq Muhammad et al.: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Leonard I. Malis, M.D., "The Value of Irrigation During Bipolar Coagulation," 1989.
McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.
http:/www.ethicon.com/GB-en/healthcare-professionals/products/energy-devices/capital//ge . . . .
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al., "Thermal Imaging in Surgery," p. 19-3, in Medical Infrared Imaging, N. A. Diakides and J. D. Bronzino, Eds. (2008).
http://www.4-traders.com/JOHNSON-JOHNSON-4832/news/Johnson-Johnson-Ethicon-E . . . .
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

(56) References Cited

OTHER PUBLICATIONS

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Douglas, S.C. "Introduction to Adaptive Filter". Digital Signal Processing Handbook. Ed. Vijay K. Madisetti and Douglas B. Williams. Boca Raton: CRC Press LLC, 1999.

Chen et al., "Heat-induced changes in the mechanics of a collagenous tissue: pseudoelastic behavior at 37° C.," Journal of Biomechanics, 31, pp. 211-216 (1998).

Kurt Gieck & Reiner Gieck, Engineering Formulas § Z.7 (7th ed. 1997).

Glaser and Subak-Sharpe, Integrated Circuit Engineering, Addison-Wesley Publishing, Reading, MA (1979). (book—not attached).

Covidien 501(k) Summary Sonicision, dated Feb. 24, 2011 (7 pages).

Lacourse, J.R .; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

\* cited by examiner

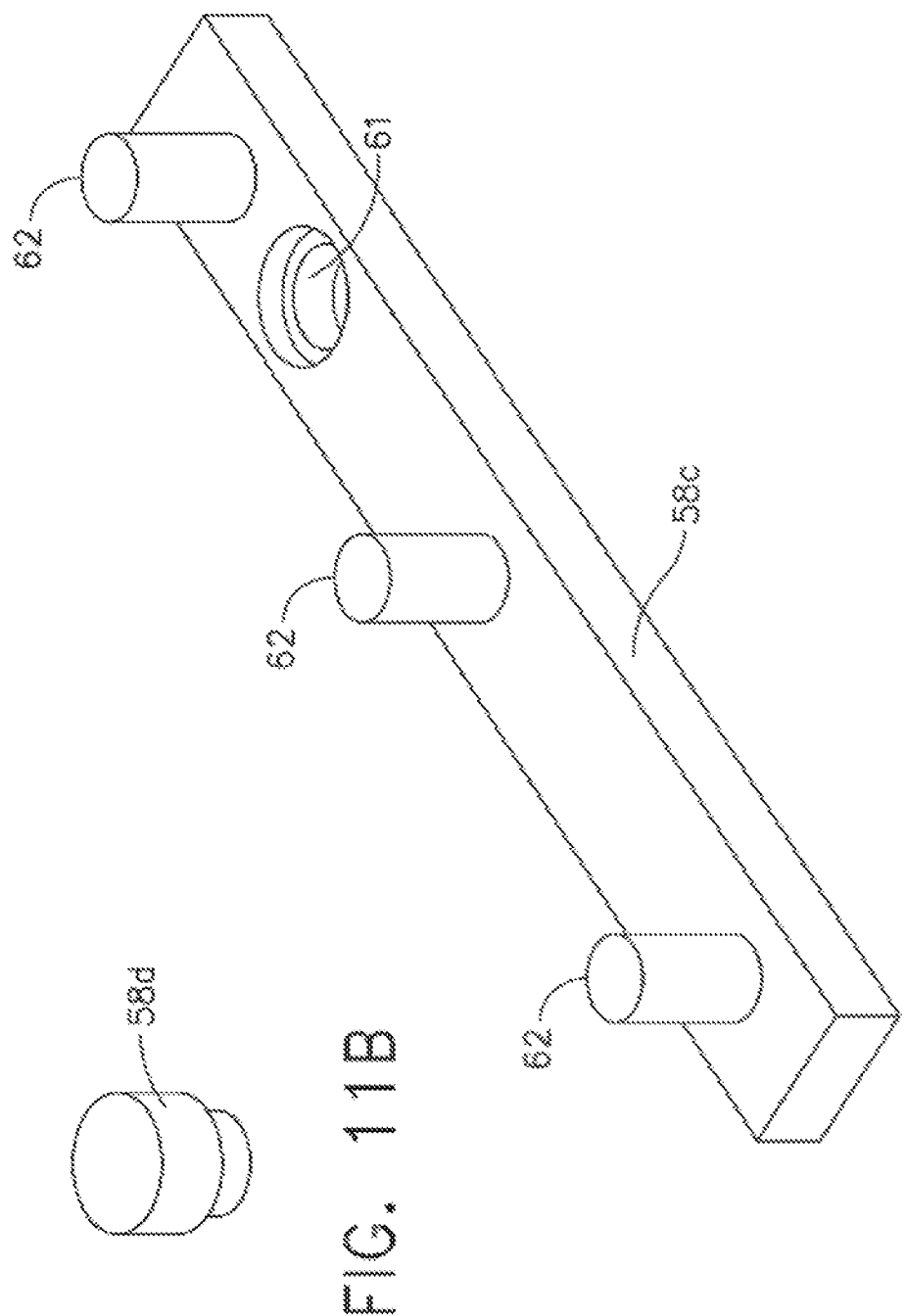

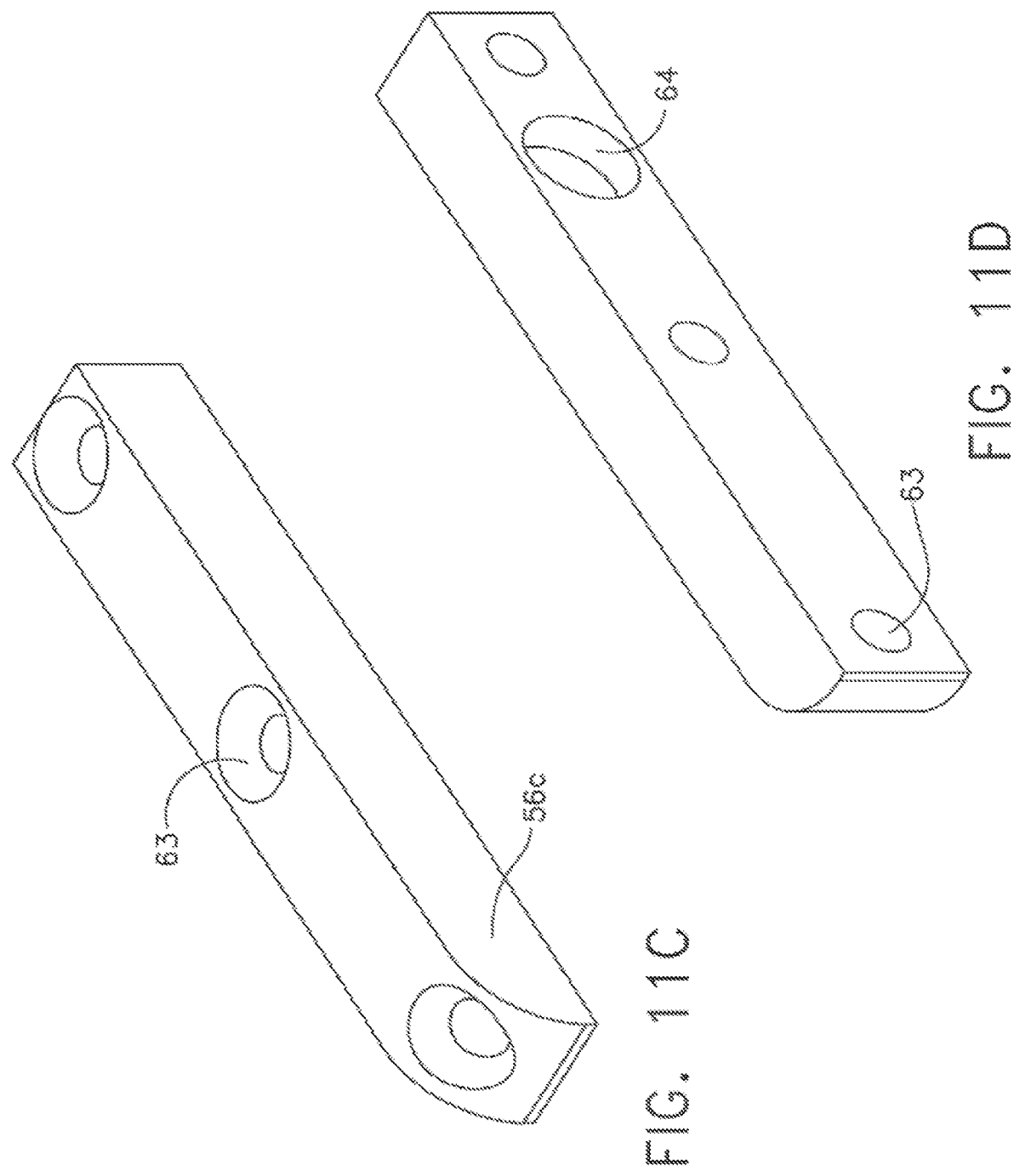

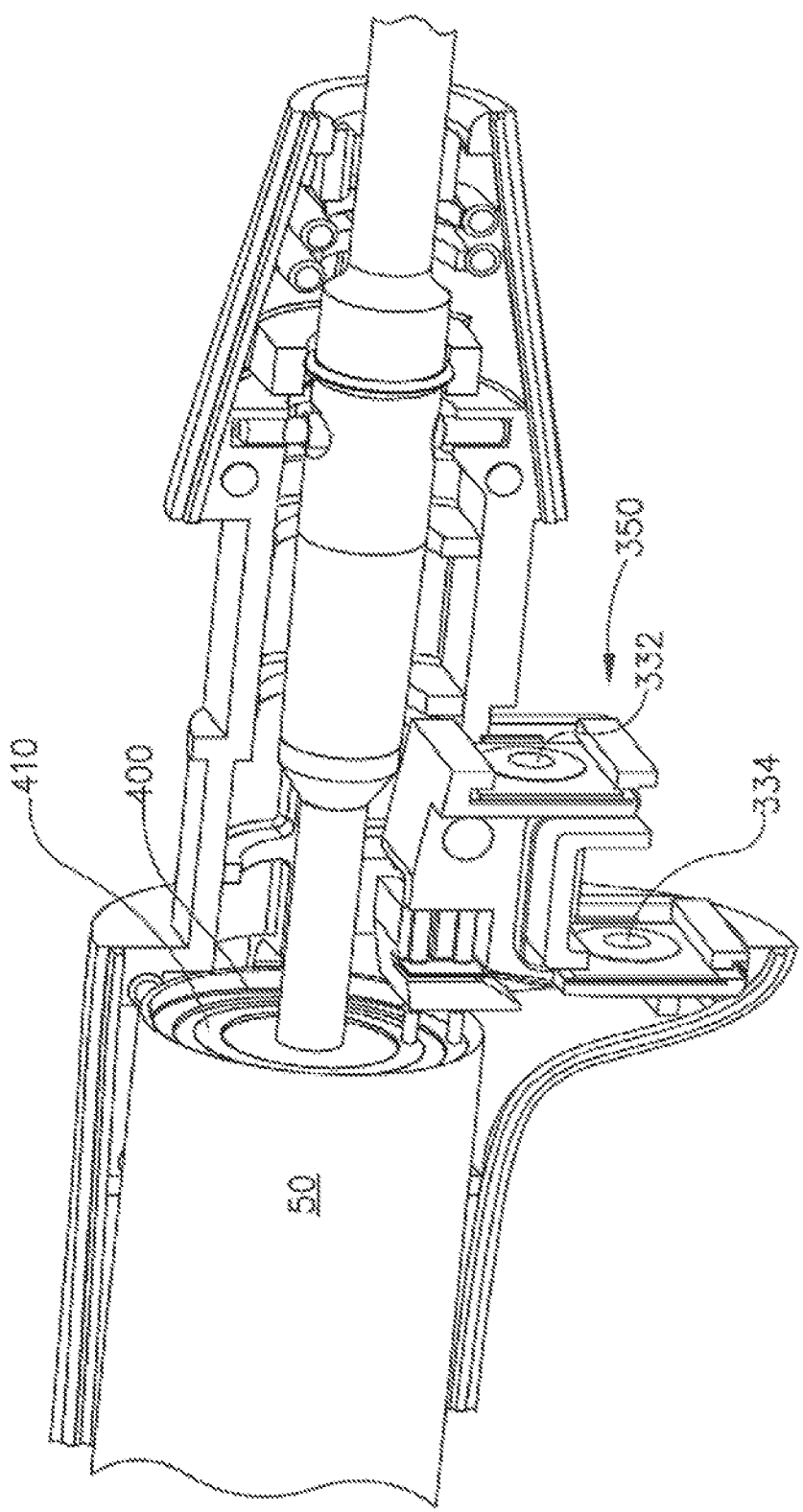

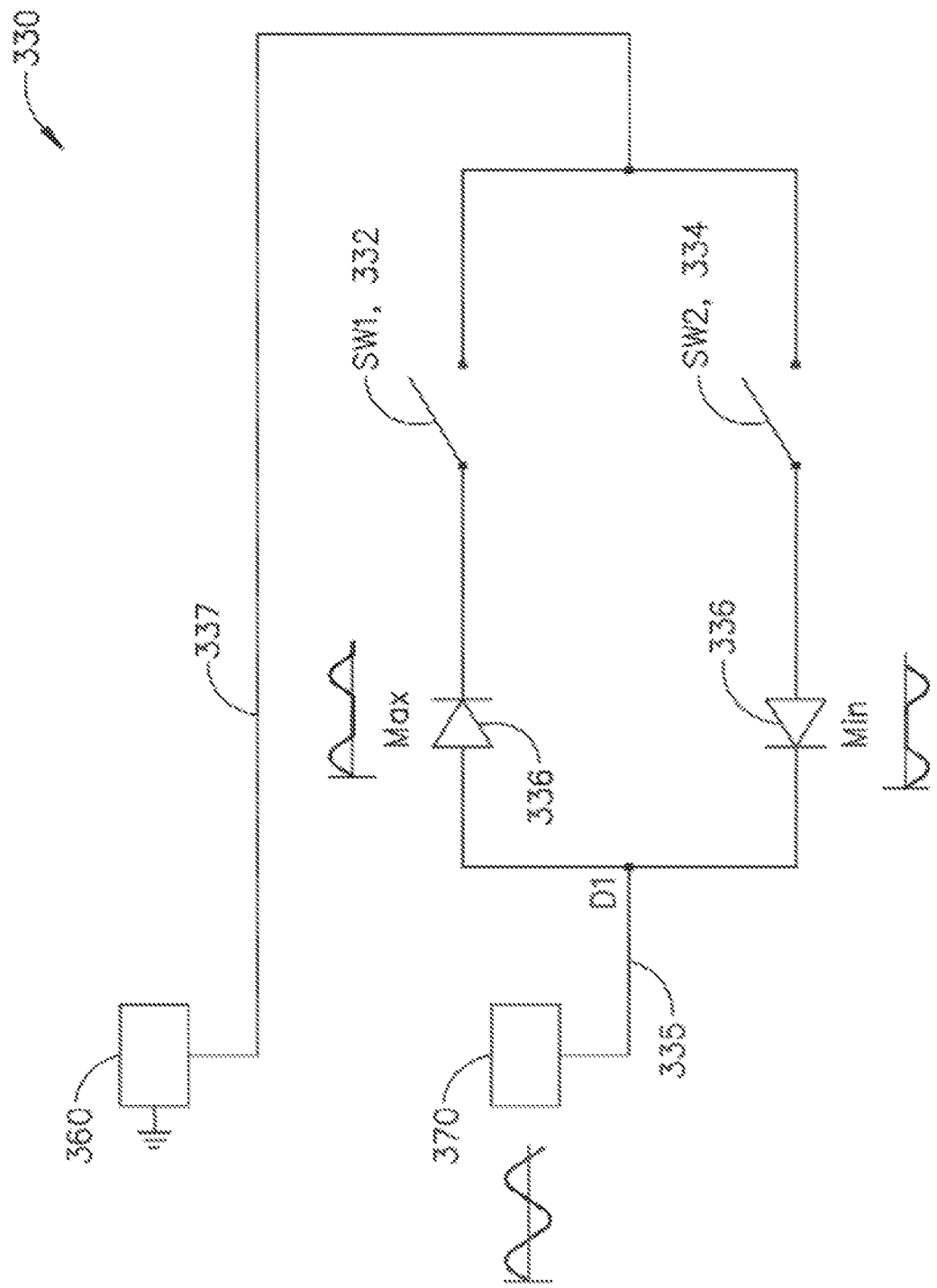

ULTRASONIC DEVICE FOR CUTTING AND COAGULATING

REFERENCE TO RELATED APPLICATIONS

This application is a continuation application claiming priority under 35 U.S.C. § 120 to U.S. patent application Ser. No. 15/690,925, entitled ULTRASONIC DEVICE FOR CUTTING AND COAGULATING, filed Aug. 30, 2017, now U.S. Patent Application Publication No. 2017/0360468, which is a continuation application claiming priority under 35 U.S.C. § 120 to U.S. patent application Ser. No. 14/223,121, entitled ULTRASONIC DEVICE FOR CUTTING AND COAGULATING, filed Mar. 24, 2014, now U.S. Patent Application Publication No. 2014/0207163, which is a continuation application claiming priority under 35 U.S.C. § 120 to U.S. patent application Ser. No. 13/311,695, entitled ULTRASONIC DEVICE FOR CUTTING AND COAGULATING, filed Dec. 6, 2011, now U.S. Patent Application Publication No. 2012/0078249, which is a divisional application claiming priority under 35 U.S.C. § 121 to U.S. patent application Ser. No. 11/548,407, entitled ULTRASONIC DEVICE FOR CUTTING AND COAGULATING, filed Oct. 11, 2006, now U.S. Patent Application Publication No. 2007/0191713, which claims the benefit of priority under 35 U.S.C. § 119(e) of U.S. Provisional Patent Application Ser. No. 60/726,625, entitled ULTRASONIC DEVICE FOR CUTTING AND COAGULATING, filed Oct. 14, 2005, the entire disclosures of which are hereby incorporated by reference herein.

FIELD OF THE INVENTION

The present invention generally relates to ultrasonic surgical systems and, more particularly, to an ultrasonic device that is optimized to allow surgeons to perform cutting, coagulation, and fine dissection required in fine and delicate surgical procedures such as a thyroidectomy.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and homeostasis by coagulation, desirably minimizing patient trauma. The cutting action is typically effected by an end-effector at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures.

Ultrasonic surgical instruments have been developed that include a clamp mechanism to press tissue against the blade of the end-effector in order to couple ultrasonic energy to the tissue of a patient. Such an arrangement (sometimes referred to as a clamp coagulator shears or an ultrasonic transector) is disclosed in U.S. Pat. Nos. 5,322,055; 5,873,873 and 6,325,811. The surgeon activates the clamp arm to press the clamp pad against the blade by squeezing on the handgrip or handle.

Some current designs of clamp coagulator shears utilize a foot pedal to energize the surgical instrument. The surgeon operates the foot pedal while simultaneously applying pressure to the handle to press tissue between the jaw and blade to activate a generator that provides energy that is transmitted to the cutting blade for cutting and coagulating tissue. Key drawbacks with this type of instrument activation include the loss of focus on the surgical field while the surgeon searches for the foot pedal, the foot pedal getting in the way of the surgeon's movement during a procedure and surgeon leg fatigue during long cases.

Various methods have been disclosed for curved end effector balancing, which include repositioning the mass along the end effector. The drawbacks of such methods are i) high stresses in the curved region, which makes the end effector more prone to fracture if it comes in contact with metal during surgery; ii) a shorter active length, which limits the vessel size that can be operated on, (the active length is defined as the length from the distal end of the blade to where the displacement is one half of the displacement at its distal end); and/or iii) the inability to separately balance orthogonal displacements.

Some current designs of clamp coagulator shears utilize handles that are either of a pistol or scissors grips design. The scissor grip designs may have one thumb or finger grip that is immovable and fixed to the housing and one movable thumb or finger grip. This type of grip may not be entirely familiar to surgeons who use other open-type surgical instruments, such as hemostats, where both thumb and finger grips move in opposition to one another. Current designs have scissor arms that rotate around a fixed pivot or rotation point that is perpendicular to the longitudinal axis of the working element. This approach is limited since the relative motion between the two arms is completely rotational. This feature limits the ability to control the pressure profile between the two working ends when fully closed.

Some current designs of clamp coagulator shears are not specifically designed for delicate procedures where precise dissection, cutting and coagulation are required. An exemplary procedure is a thyroidectomy where precise dissection, cutting and coagulation is required to avoid critical blood vessels and nerve bundles.

It would be desirable to provide an ultrasonic surgical instrument that overcomes some of the deficiencies of current instruments. The ultrasonic surgical instrument described herein overcomes those deficiencies.

BRIEF DESCRIPTION OF THE FIGURES

The novel features of the invention are set forth with particularity in the appended claims. The invention itself, however, both as to organization and methods of operation, may best be understood by reference to the following description, taken in conjunction with the accompanying drawings in which:

FIG. 11A-B are an alternate expressions for a first and second tissue pad;

FIG. 11C is a perspective view of an alternate expression of a clamp arm for use with the tissue pads of FIGS. 11A-B;

FIG. 11D is an alternate view of the clamp are of FIG. 11C;

FIG. 16C is a cut-away elevation view showing the interface among the switch housing, transducer, waveguide and housing;

FIG. 16G is an electrical schematic of the hand switch circuit;

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

The present invention is particularly directed to an improved ultrasonic surgical clamp coagulator apparatus which is configured for effecting tissue cutting, coagulation, and/or clamping during surgical procedures, including delicate surgical procedures, such as a thyroidectomy. The present apparatus is configured for use in open surgical procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

As will become apparent from the following description, the present clamp coagulator apparatus is particularly configured for disposable use by virtue of its straightforward construction. As such, it is contemplated that the apparatus be used in association with an ultrasonic generator unit of a surgical system, whereby ultrasonic energy from the generator unit provides the desired ultrasonic actuation for the present clamp coagulator apparatus. It will be appreciated that a clamp coagulator apparatus embodying the principles of the present invention can be configured for non-disposable or multiple use, and non-detachably integrated with an associated ultrasonic generator unit. However, detachable connection of the present clamp coagulator apparatus with an associated ultrasonic generator unit is presently preferred for single-patient use of the apparatus.

Figure 1:
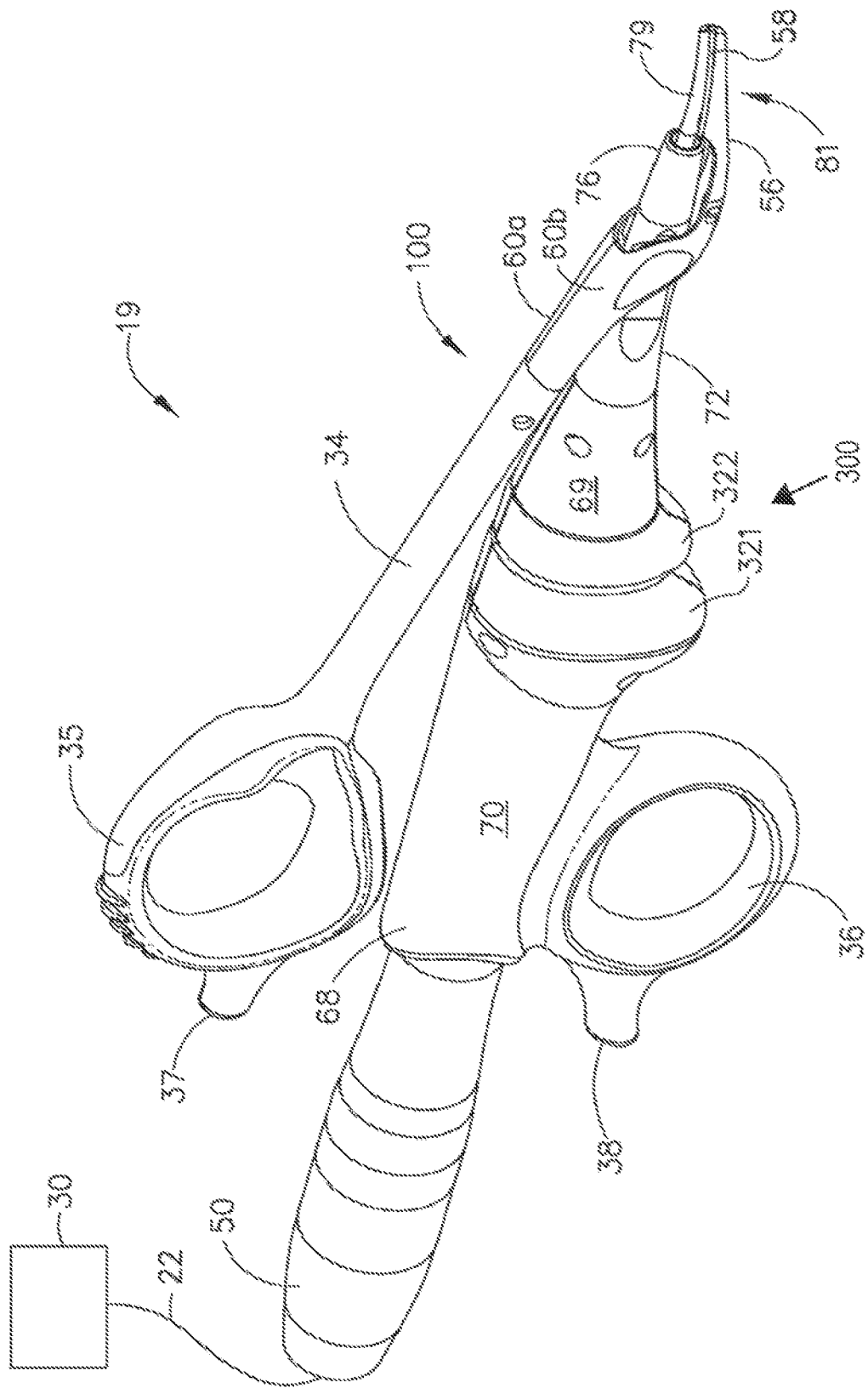
FIG. 1 is a perspective view illustrating an embodiment of an ultrasonic surgical instrument in accordance with the present invention.
Figure 2:
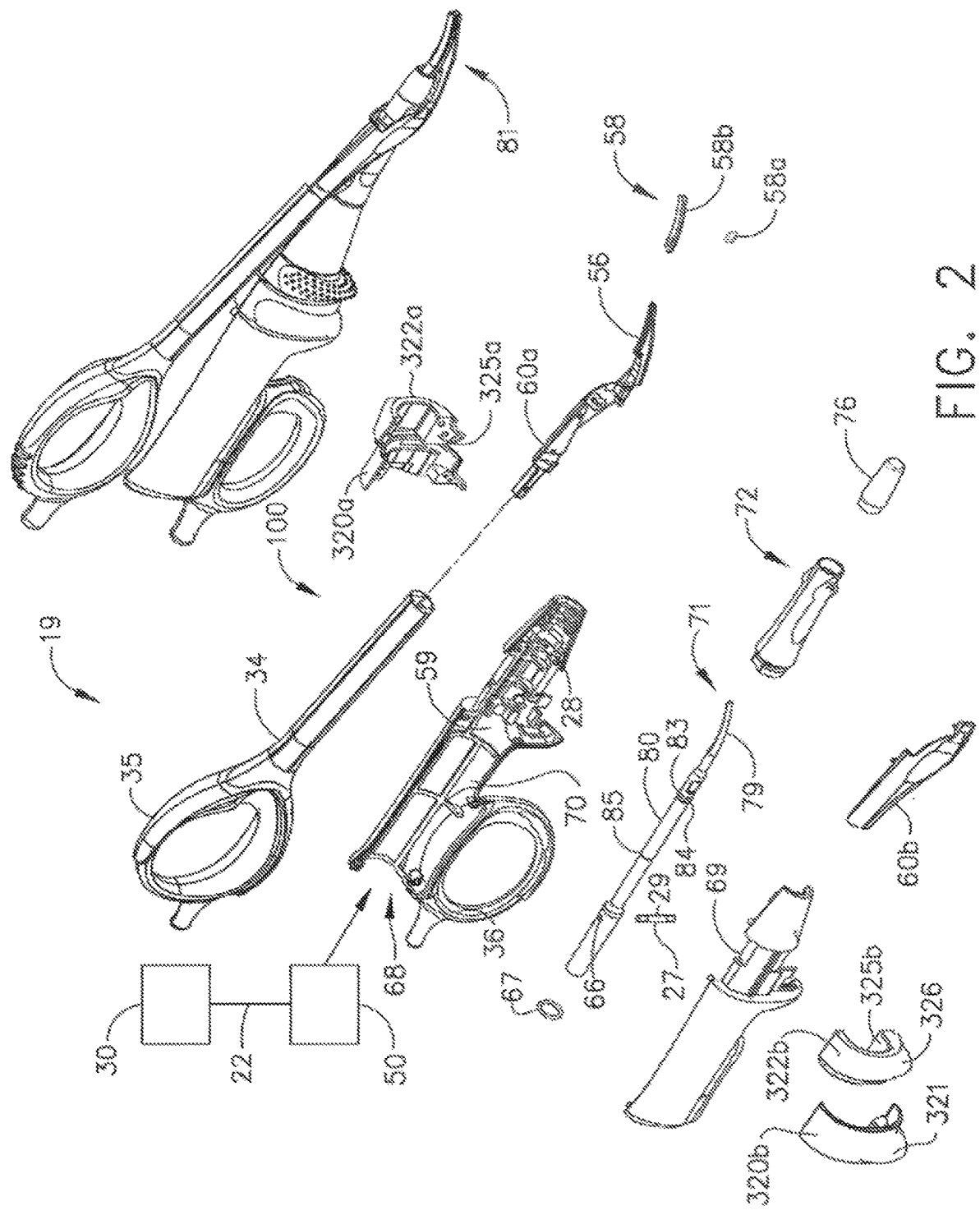
FIG. 2 is a perspective assembly view of FIG. 1.

With specific reference now to FIGS. 1 and 2, an embodiment of a surgical system 19, including an ultrasonic surgical instrument 100 in accordance with the present invention is illustrated. The surgical system 19 includes an ultrasonic generator 30 connected to an ultrasonic transducer 50 via cable 22, and an ultrasonic surgical instrument 100. It will be noted that, in some applications, the ultrasonic transducer 50 is referred to as a "hand piece assembly" because the surgical instrument of the surgical system 19 is configured such that a surgeon may grasp and manipulate the ultrasonic transducer 50 during various procedures and operations. A suitable generator is the GEN04 (also referred to as Generator 300) sold by Ethicon Endo-Surgery, Inc. of Cincinnati, Ohio. A suitable transducer is disclosed in co-pending U.S. patent application filed on Oct. 10, 2006, Ser. No. 11/545,784, now U.S. Pat. No. 8,152,825, entitled MEDICAL ULTRASOUND SYSTEM AND HANDPIECE AND METHODS FOR MAKING AND TUNING, the contents which are incorporated by reference herein.

Ultrasonic transducer 50, and an ultrasonic waveguide 80 together provide an acoustic assembly of the present surgical system 19, with the acoustic assembly providing ultrasonic energy for surgical procedures when powered by generator 30. The acoustic assembly of surgical instrument 100 generally includes a first acoustic portion and a second acoustic portion. In the present embodiment, the first acoustic portion comprises the ultrasonically active portions of ultrasonic transducer 50, and the second acoustic portion comprises the ultrasonically active portions of transmission assembly 71. Further, in the present embodiment, the distal end of the first acoustic portion is operatively coupled to the proximal end of the second acoustic portion by, for example, a threaded connection.

The ultrasonic surgical instrument 100 includes a multi-piece handle assembly 68 adapted to isolate the operator from the vibrations of the acoustic assembly contained within transducer 50. The handle assembly 68 can be shaped to be held by a user in a conventional manner, but it is contemplated that the present ultrasonic surgical instrument 100 principally be grasped and manipulated in a scissor-like arrangement provided by a handle assembly of the instrument, as will be described. While multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer into the handle assembly 68. The ultrasonic surgical instrument 100 may be attached to and removed from the ultrasonic transducer 50 as a unit. The ultrasonic surgical instrument 100 may include a handle assembly 68, comprising mating housing portions 69 and 70 and an ultrasonic transmission assembly 71. The elongated transmission assembly 71 of the ultrasonic surgical instrument 100 extends orthogonally from the instrument handle assembly 68.

The handle assembly 68 may be constructed from a durable plastic, such as polycarbonate or a liquid crystal polymer. It is also contemplated that the handle assembly 68 may alternatively be made from a variety of materials including other plastics, ceramics or metals. Traditional unfilled thermoplastics, however, have a thermal conductivity of only about 0.20 W/m° K (Watt/meter-° Kelvin). In order to improve heat dissipation from the instrument, the handle assembly may be constructed from heat conducting thermoplastics, such as high heat resistant resins liquid crystal polymer (LCP), Polyphenylene Sulfide (PPS), Polyetheretherketone (PEEK) and Polysulfone having thermal conductivity in the range of 20-100 W/m° K. PEEK resin is a thermoplastics filled with aluminum nitride or boron nitride, which are not electrically conductive. The thermally conductive resin helps to manage the heat within smaller instruments.

The transmission assembly 71 includes a waveguide 80 and a blade 79. It will be noted that, in some applications, the transmission assembly is sometimes referred to as a "blade assembly". The waveguide 80, which is adapted to transmit ultrasonic energy from transducer 50 to the tip of blade 79 may be flexible, semi-flexible or rigid. The waveguide 80 may also be configured to amplify the mechanical vibrations transmitted through the waveguide 80 to the blade 79 as is well known in the art. The waveguide 80 may further have features to control the gain of the longitudinal vibration along the waveguide 80 and features to tune the waveguide 80 to the resonant frequency of the system In particular, waveguide 80 may have any suitable cross-sectional dimension. For example, the waveguide 80 may have a substantially uniform cross-section or the waveguide 80 may be tapered at various sections or may be tapered along its entire length.

Ultrasonic waveguide 80 may, for example, have a length substantially equal to an integral number of one-half system wavelengths (nλ/2). The ultrasonic waveguide 80 and blade 79 may be preferably fabricated from a solid core shaft constructed out of material, which propagates ultrasonic energy efficiently, such as titanium alloy (i.e., Ti-6Al-4V), aluminum alloys, sapphire, stainless steel or any other acoustically compatible material.

Ultrasonic waveguide 80 may further include at least one radial hole or aperture 66 extending therethrough, substantially perpendicular to the longitudinal axis of the waveguide 80. The aperture 66, which may be positioned at a node, is configured to receive a connector pin 27, discussed below, which connects the waveguide 80, to the handle assembly 70.

Blade 79 may be integral with the waveguide 80 and formed as a single unit. In an alternate expression of the current embodiment, blade 79 may be connected by a threaded connection, a welded joint, or other coupling mechanisms. The distal end of the blade 79 is disposed near an anti-node 85 in order to tune the acoustic assembly to a preferred resonant frequency $f_o$ when the acoustic assembly is not loaded by tissue. When ultrasonic transducer 50 is energized, the distal end of blade 79 or blade tip 79a is configured to move substantially longitudinally (along the x axis) in the range of, for example, approximately 10 to 500 microns peak-to-peak, and preferably in the range of about 20 to about 200 microns at a predetermined vibrational frequency $f_o$ of, for example, 55,500 Hz. Blade tip 79a also preferably vibrates in the y axis at about 1 to about 10 percent of the motion in the x axis.

The blade tip 79a provides a functional asymmetry or curved portion for improved visibility at the blade tip so that a surgeon can verify that the blade 79 extends across the structure being cut or coagulated. This is especially important in verifying margins for large blood vessels. The geometry also provides for improved tissue access by more closely replicating the curvature of biological structures. Blade 79 provides a multitude of edges and surfaces, designed to provide a multitude of tissue effects: clamped coagulation, clamped cutting, grasping, back-cutting, dissection, spot coagulation, tip penetration and tip scoring.

Blade tip 79a is commonly referred to as a functional asymmetry. That is, the blade (functionally, the blade provides a multitude of tissue effects) lies outside the longitudinal axis of waveguide 80 (that is, asymmetrical with the longitudinal axis), and accordingly creates an imbalance in the ultrasonic waveguide. If the imbalance is not corrected, then undesirable heat, noise, and compromised tissue effect occur.

It is possible to minimize unwanted tip excursion in the y and z axes, and therefore maximize efficiency with improved tissue effect, by providing one or more balance asymmetries or balancing features proximal to the blade functional asymmetry.

Referring now to FIGS. 3A-G, transmission assembly 71 includes one or more balancing features placed at blade 79, at a position proximal and/or distal to the distal most node 84. In addition, the balancing features at the waveguide 80 are shaped to balance the two orthogonal modes in the y and z axes, separately. The size and shape and location of the balance features allow flexibility to reduce stress at the blade 79, make the active length longer and separately balance the two orthogonal modes.

Figure 3A:
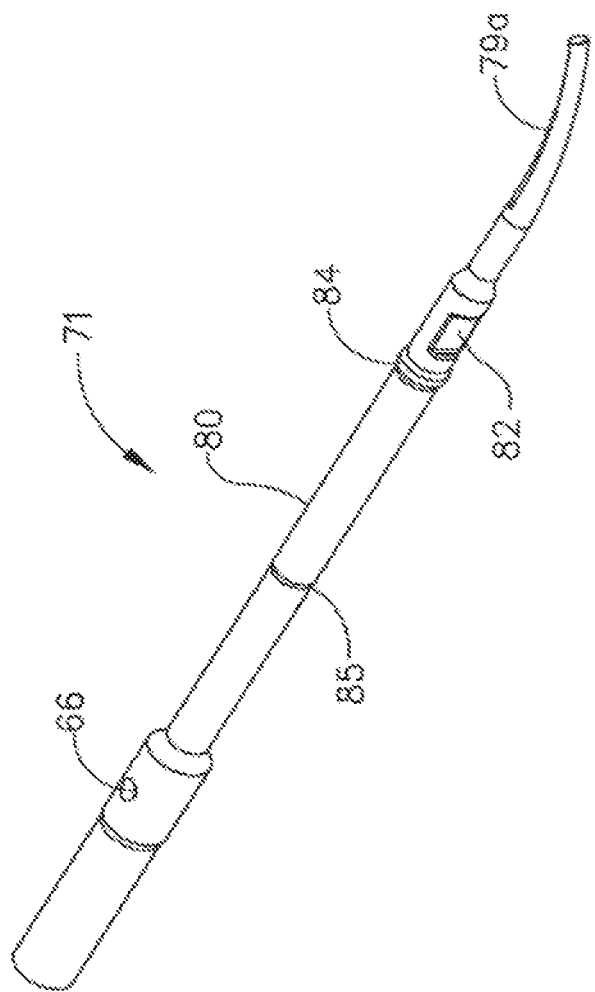
FIG. 3A is a perspective view of one embodiment of a waveguide and blade in accordance with the present invention.
Figure 3B:
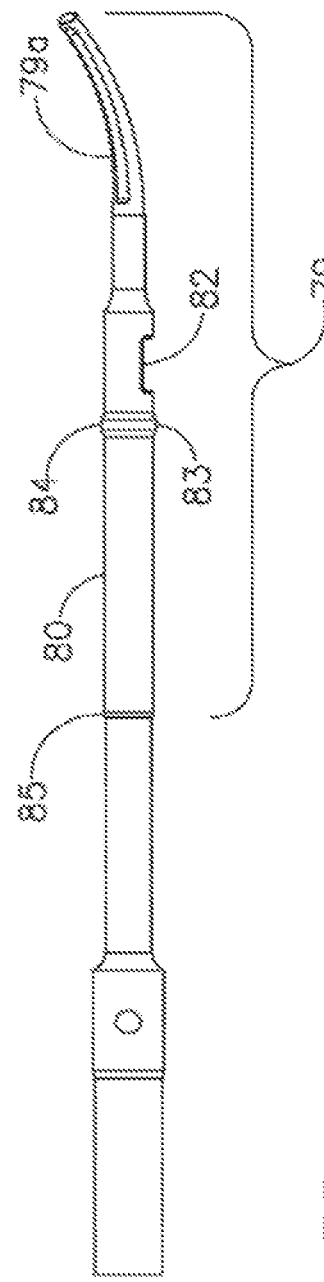
FIG. 3B is an elevation view of the waveguide and blade of FIG. 3A.

FIGS. 3A-B show a single balance cut 82 at the waveguide 80 distal to node 84. In this embodiment balance cut 82 has side walls perpendicular to the longitudinal axis of waveguide 80 and the bottom cut is parallel to the longitudinal axis of waveguide 80. In this embodiment the high stresses experienced during operation are localized at the balancing cut 82, which is away from the more sensitive curved region at the blade 79.

Figure 3C:
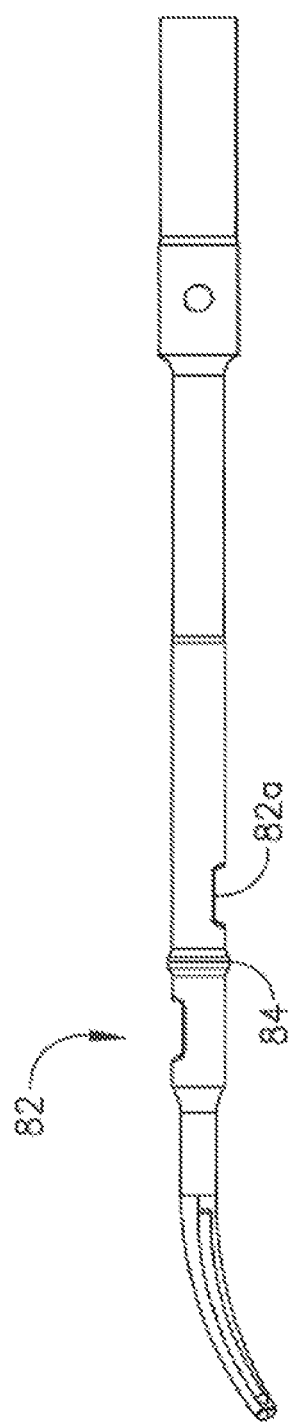
FIG. 3C is an elevation view of an alternate embodiment of a waveguide and blade in accordance with the present invention.

FIG. 3C shows two balancing features 82 and 82a, one distal and one proximal to the node 84. Adding second balance cut 82a, proximal to node 84 further eliminates the orthogonal bending modes thereby providing a more pure longitudinal motion (x direction) and removing the overlapping bending modes (y and z direction). Accordingly, the blade 79 is better balanced and has a longer active length.

Figure 3D:
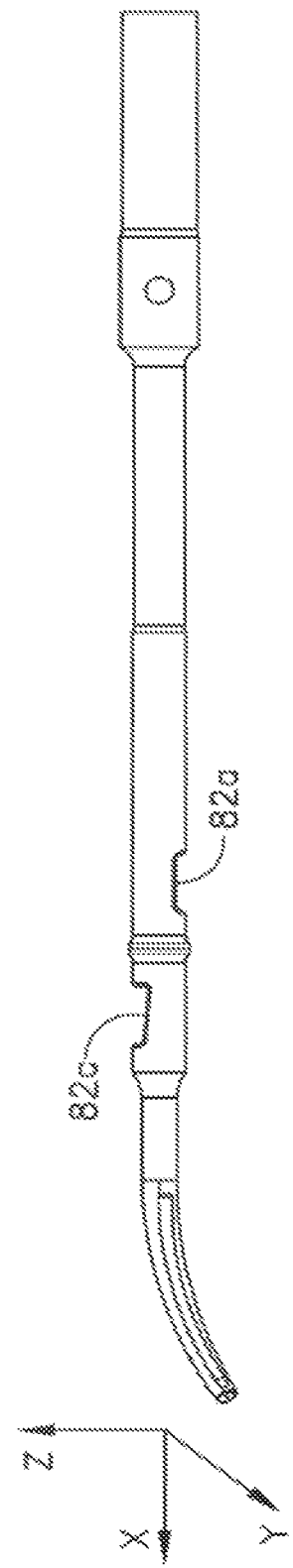
FIG. 3D is an elevation view of an alternate embodiment of a waveguide and blade in accordance with the present invention.

FIG. 3D shows two balancing features 82c and 82a, distal and proximal to the node 84. An angled bottom cut at balance feature 82c allows individual balancing of the bending mode in the z direction.

Figure 3E:
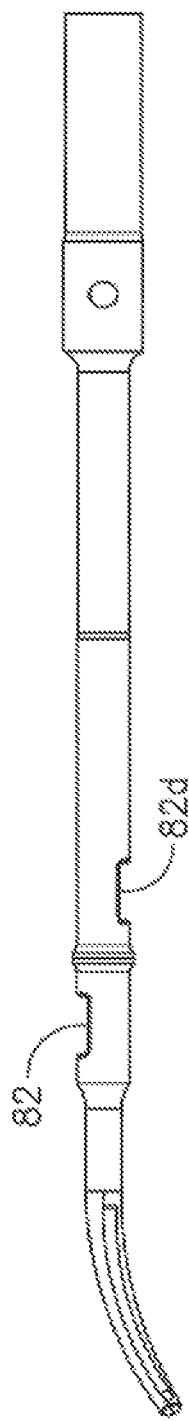
FIG. 3E is an elevation view of an alternate embodiment of a waveguide and blade in accordance with the present invention.
Figure 3F:
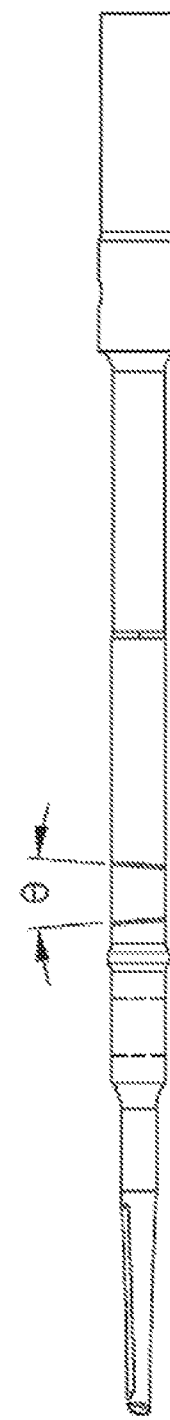
FIG. 3F is an alternate view of the embodiment of the waveguide and blade of FIG. 3E.

FIGS. 3E-F show two balancing features 82 and 82d, distal and proximal to the node 84. The side walls of balance feature 82d are angled with respect to each other in the x-z plane and provide for individual balancing of the bending mode in they direction. The angled side walls define an included angle θ of between 1° and about 90°, preferably between about 15° and about 25°, and more preferably between about 19° and about 21°. The weight removed at each balance feature is a function of multiple parameters including the radius of curvature at blade tip 79a and the desired level of removal of the overlapping bending modes in the y and z direction. In an illustrative example, the balance cut 82 represents a weight reduction of about 0.003 to about 0.004 oz., and most preferably about 0.0034 oz. The balance cut 82d represents a weight reduction of about 0.004 to about 0.005 oz., and most preferably about 0.0043 oz.

Figure 3G:
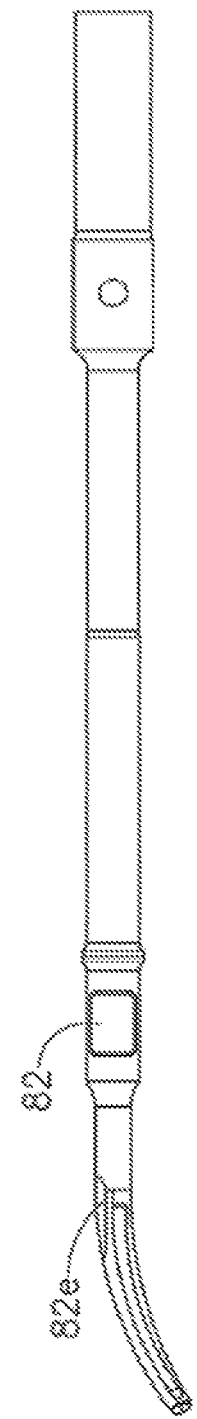
FIG. 3G is an elevation view of an alternate embodiment of a waveguide and blade in accordance with the present invention.

FIG. 3G shows one balance cut 82e in the curved blade region in addition to balance feature 82, distal to node 84. Balance cut 82e allows for balancing as well as improved acoustic performance as a result of wide frequency separation of transverse modes from the fundamental frequency, which is the longitudinal mode frequency.

As would be apparent to one skilled in the art, any combination of balance cuts 82 through 82e are possible to provide balancing of a waveguide and curved blade.

Figure 4:
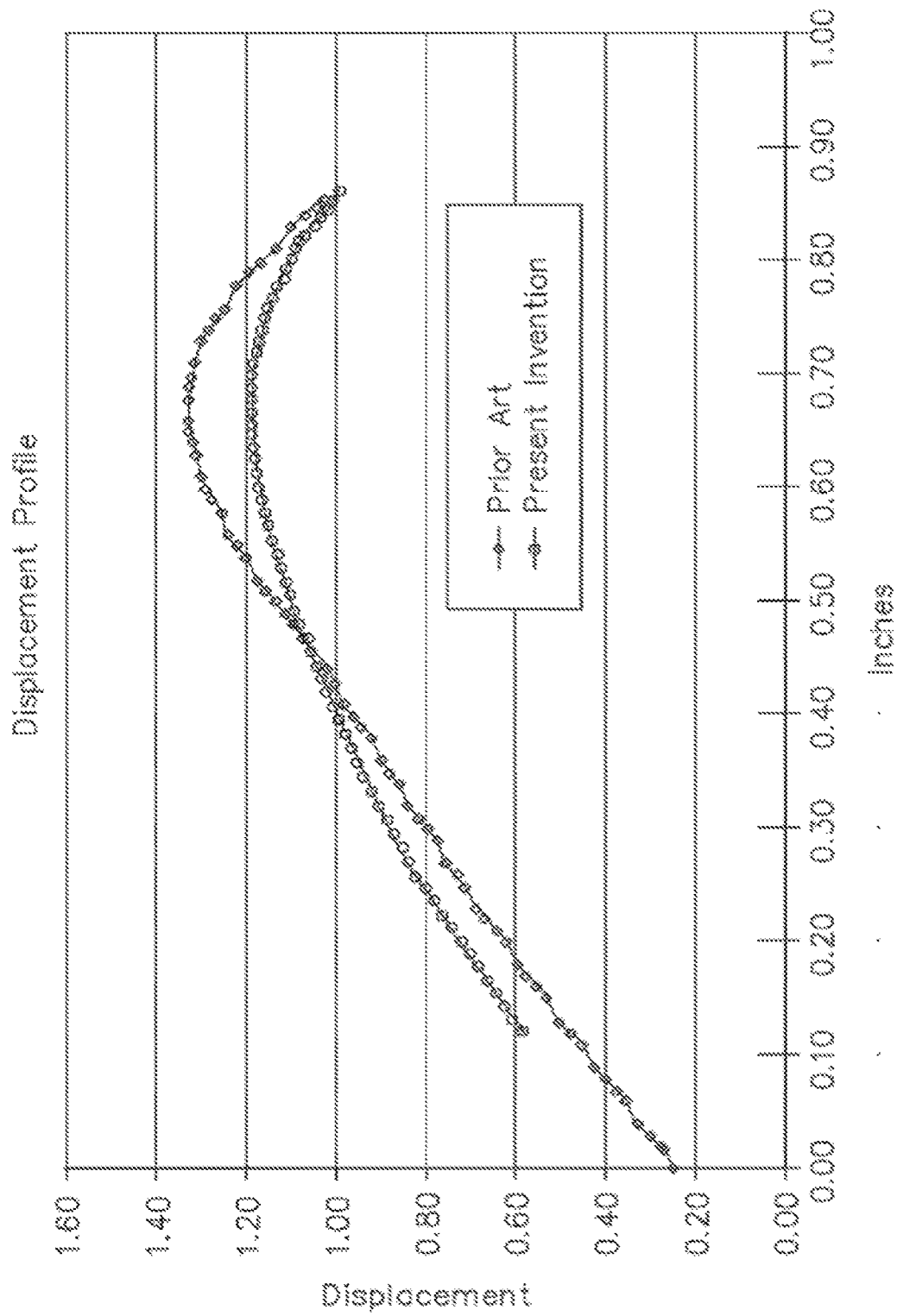
FIG. 4 is a graph illustrating the displacement profile of the present invention and the prior art.

FIG. 4 shows that the profile produced by the balancing cut features of FIG. 3E produces a 1.3 mm longer active length along the longitudinal displacement direction than is available from an LCS-C5 ultrasonic clamp coagulator, sold by Ethicon Endo-Surgery, Inc. (where they axis is representative of the ratio between the displacement anywhere along blade tip 79a and the displacement at the most distal end of blade tip 79a). A longer active length is desirable for cutting and coagulating large vessels, for example, 5-7 mm vessels.

Figure 5:
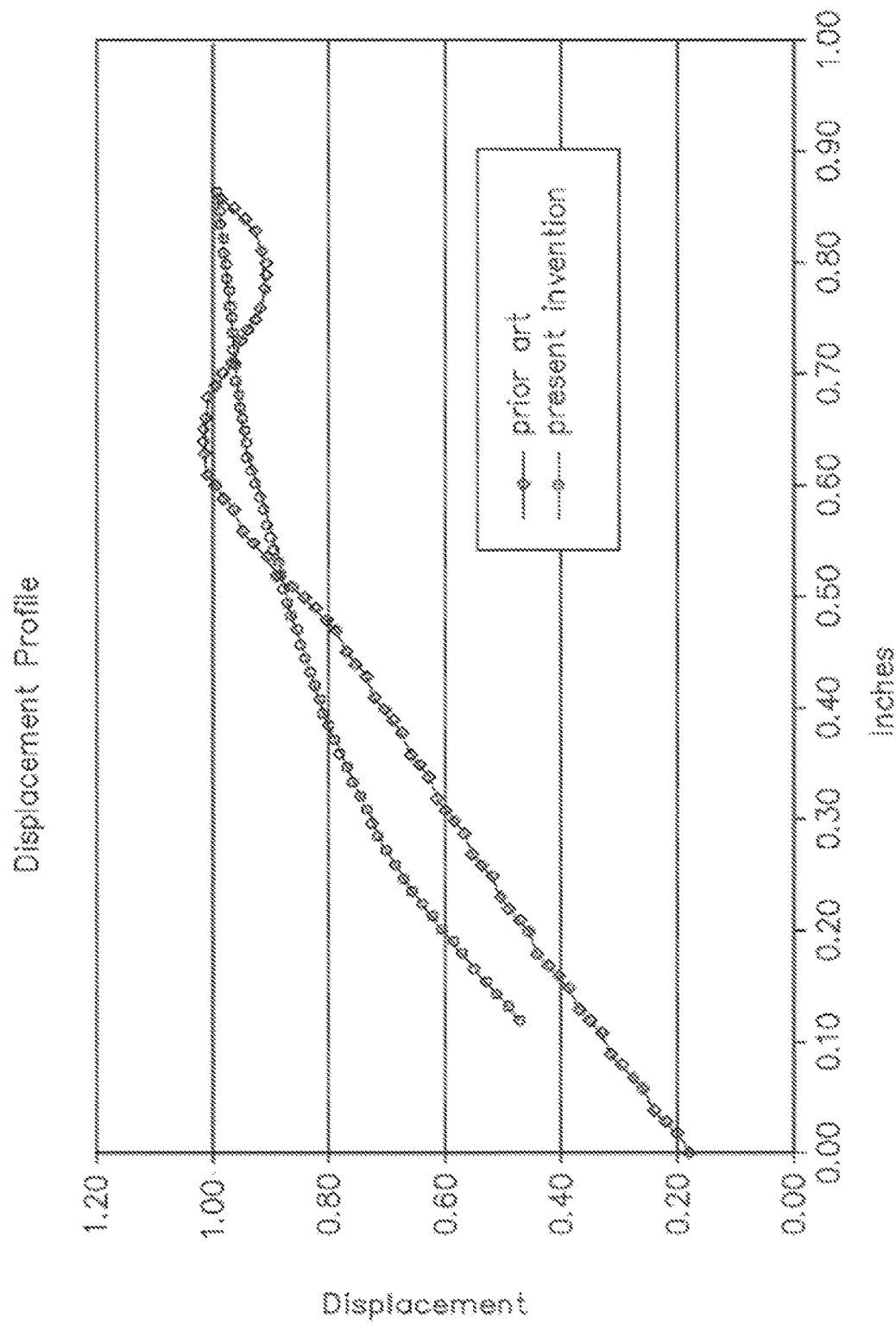
FIG. 5 is a graph illustrating an alternate displacement profile of the present invention and the prior art.

FIG. 5 shows that the profile produced by the balancing features of FIG. 3E produces a 2.5 mm longer active length (along the vector sum of displacements in the x, y and z directions) than is available from an LCS-C5 ultrasonic clamp coagulator, which is desirable for cutting and coagulating large vessels, for example, 5-7 mm vessels.

Referring back to FIGS. 1 and 2 an outer tubular member or outer shroud 72 attaches to the most proximal end of handle assembly 70. Attached to the distal end of the outer shroud 72 is a distal shroud 76. Both the outer shroud 72 and distal shroud 76 may attach via a snap fit, press fit, glue or other mechanical means. Extending distally from the distal shroud 76 is the end-effector 81, which comprises the blade 79 and clamp member 56, also commonly referred to as a jaw, in combination with one or more tissue pads 58. A seal 83 may be provided at the distal-most node 84, nearest the end-effector 81, to abate passage of tissue, blood, and other material in the region between the waveguide 80 and the distal shroud 76. Seal 83 may be of any known construction, such as an o-ring or silicon overmolded at node 84.

Referring now to FIGS. 6A-D and 7A-B, blade 79 is curved along with the associated clamp member 56. This is illustrative only, and blade 79 and a corresponding clamp member 56 may be of any shape as is known to the skilled artisan. One benefit of the invention, however, is the ability to perform finer, more delicate surgical procedures. It is also multifunctional and able to dissect tissue as well as coagulate and transect.

The ability to finely dissect is enabled primarily by the tapering of the end effector 81. The end effector is tapered in two planes, which mimics typical hemostats. This allows the user to create windows in the tissue and then spread the tissue apart more easily. The blade 79 and clamp member 56 are tapered in both the x and z directions from the proximal end to the distal end. The pad 58 is only tapered in the Z direction. That is, the clamp pad 58 has a constant thickness, but the width of the clamp pad 58 at the distal end is less than the width at the proximal end. Accordingly, the surface area of section A is greater than the surface area of section B.

In addition to the taper, the radius at the distal end of the blade 79 and clamp member 56 also promotes fine dissection. The radius at the tip of the clamp member 56 is approximately 0.040 inches, and the blade radius is approximately 0.045 inches.

Figure 6A:
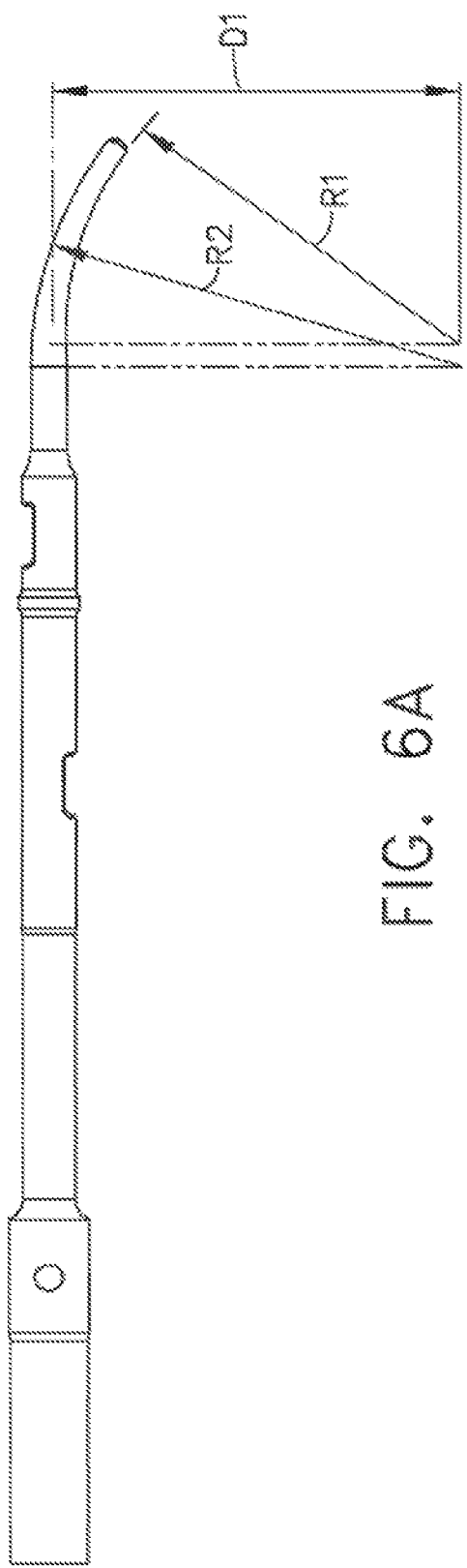
FIG. 6A is an elevation view of the waveguide and blade of FIGS. 3E-F illustrating one embodiment of the radius of curvature of the blade.

With specific reference to FIG. 6A, blade 79 is defined by an inside radius R1 and an outside radius R2 measured at a distance D1 from the longitudinal axis. The dimensions R1, R2 and D1 are selected in combination with the balance cuts previously discussed. In one embodiment R1 is from about 0.80 inches to about 1.00 inches and most preferably about 0.95 inches; R2 is from about 0.90 inches to about 1.10 inches and most preferably about 1.04 inches; and D1 is from about 0.90 inches to about 1.10 inches and most preferably about 0.99 inches.

Figure 6C:
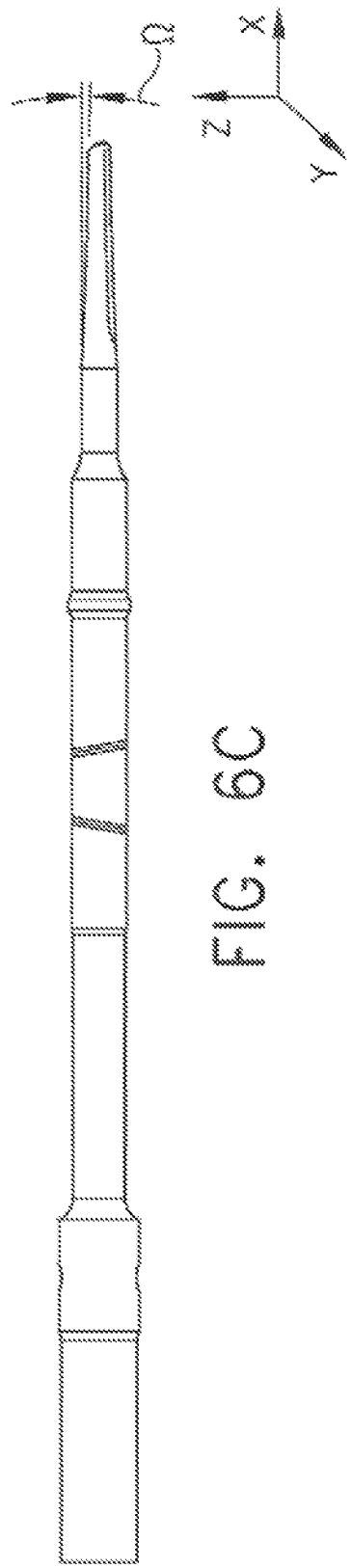
FIG. 6C is an alternate view of the embodiment of FIG. 6A.
Figure 6B:
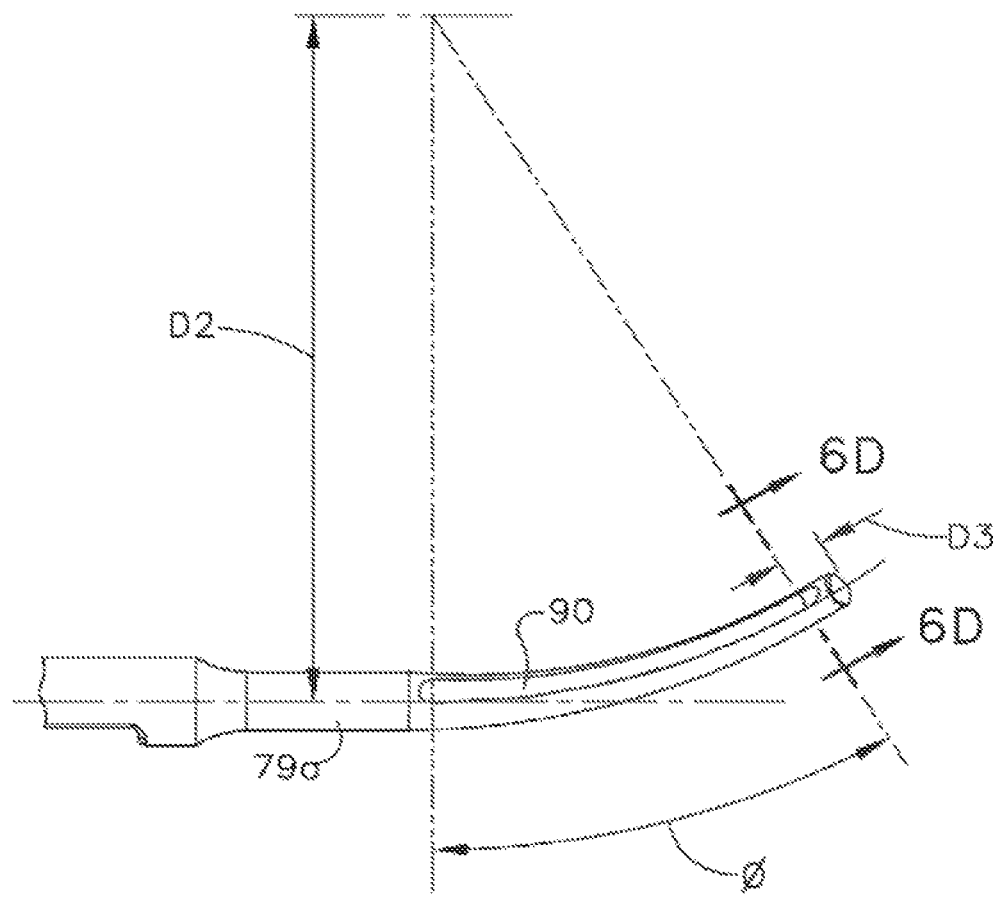
FIG. 6B is an exploded view of one embodiment of the blade of FIG. 6A and a radius cut.
Figure 6D:
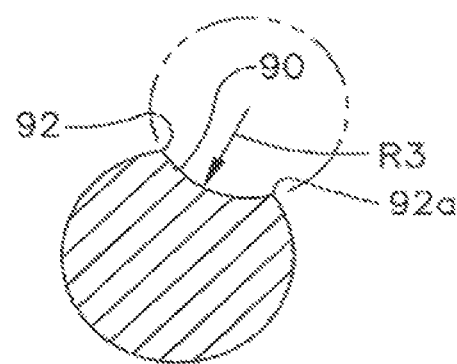
FIG. 6D is a section view of the embodiment of FIG. 6B.

FIGS. 6B and 6D further illustrate a second expression of the blade 79. Illustrated is a radius cut 90 in blade 79 to provide two back cutting edges 92 and 92a. As will be appreciated by the skilled artesian, radius cut 90 also provides a balance asymmetry within the functional symmetry to help balance the orthogonal modes. The back cutting edges 92 and 92a are positioned opposite the clamp pad 58 (FIG. 7B) to allow the surgeon to perform tissue cutting procedures without the assistance of the clamp pad 58. Preferably, the radius cut is distal to the most distal tip of blade 79 to allow for a blunt radius tip for tissue dissection as discussed above. In one example of the second expression of blade 79, a radius cut R3 is swept across an angle θ measured at a distance D2 from the longitudinal axis and starting a distance D3 from the distal tip of blade 79. In one embodiment R3 is from about 0.030 inches to about 0.060 inches and most preferably about 0.050 inches; angle θ is from about 20° to about 35° and most preferably about 30°; D2 is about 0.90 inches to about 1.10 inches and most preferably about 0.99 inches; and D3 is from about 0.085 inches to about 0.11 inches and most preferably about 0.09 inches.

Figure 7A:
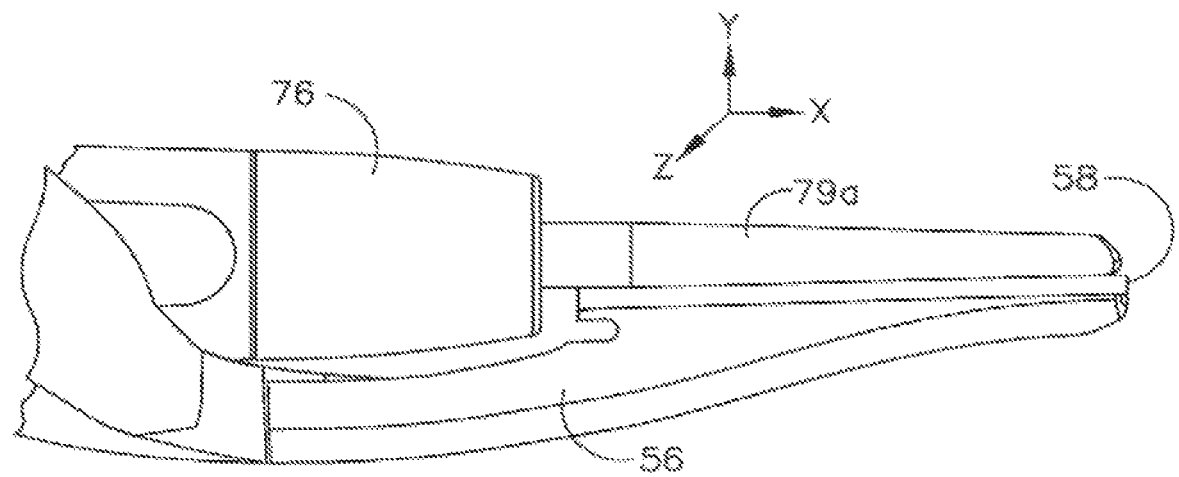
FIG. 7A is an elevation view of an end effector in accordance with the present invention.
Figure 7B:
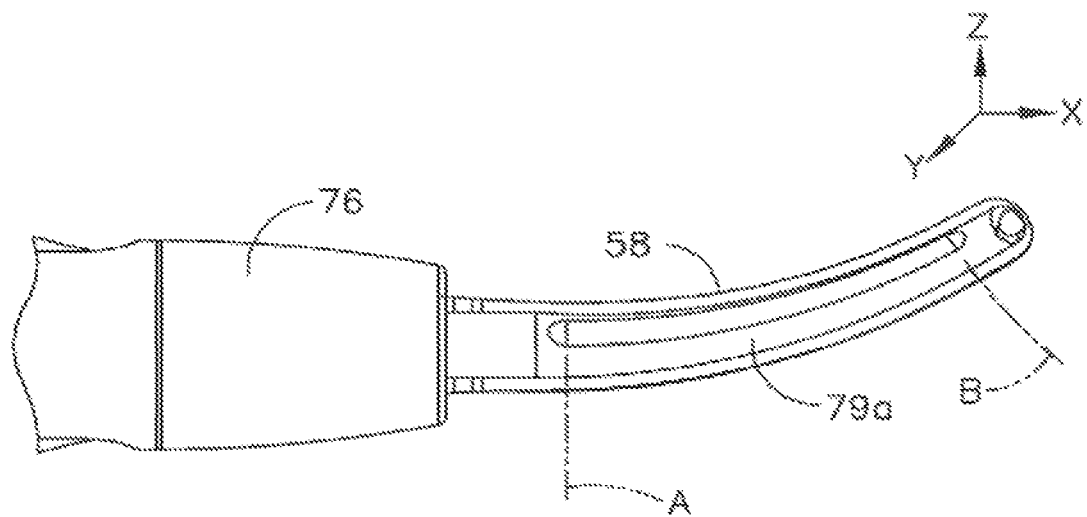
FIG. 7B is a plan view of the end effector of FIG. 7A.
Figure 8:
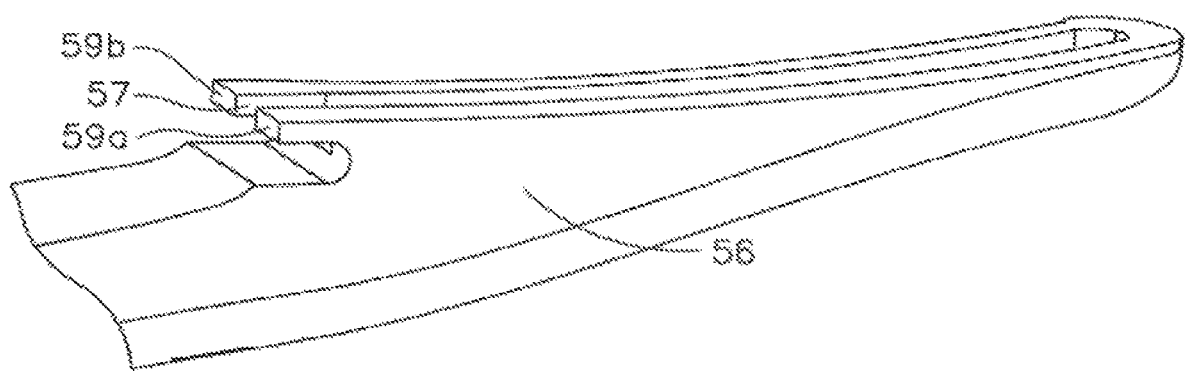
FIG. 8 is a perspective view from proximal to distal end of a clamp member in accordance with the present invention.
Figure 9A:
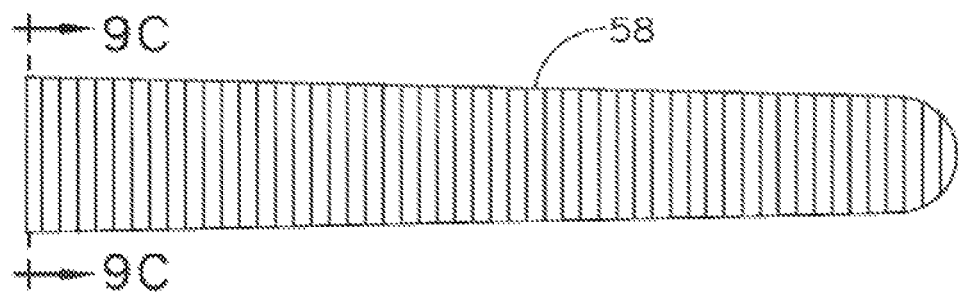
FIG. 9A is a plan view of a tissue pad in accordance with the present invention.
Figure 9B:
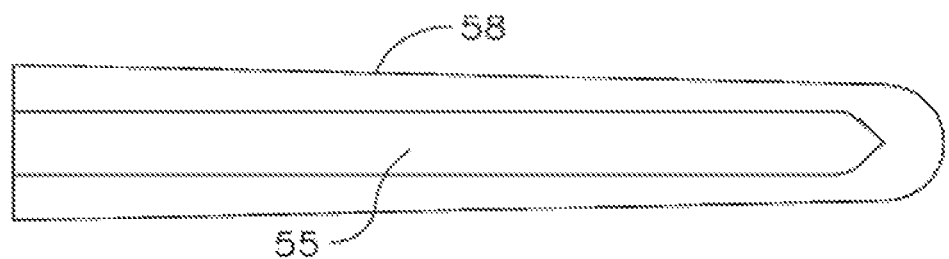
FIG. 9B is a plan view of the opposite face of the tissue pad of FIG. 9A.
Figure 9C:
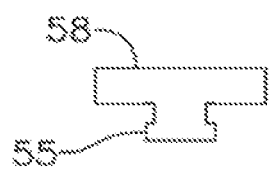
FIG. 9C is an elevation view the tissue pad of FIGS. 9A-B.

In a third expression of blade 79, FIG. 6C illustrates a taper defined by angle Ω relative to an axis parallel to the longitudinal axis of waveguide 80 from the proximal end of blade 79 to the distal end of blade 79. In one embodiment the taper may be on the blade surface that contacts tissue pad 58 (FIG. 7A). Alternatively, the taper may be the defined by the opposite surface comprising radius cut 90. Referring to FIG. 6C, angle Π ranges from about 0.5° to about 5°, and preferably from about 1.5° to about 2°.

Referring back to FIG. 2, waveguide 80 is positioned within cavity 59 of handle assembly 68. In order to properly locate the waveguide 80 both axially and radially, pin 27 extends through opening 66 of waveguide 80 (located at a node) and engages channel 28 (formed by the mating of housing portions 69 and 70). Preferably pin 27 is made of any compatible metal, such as stainless steel or titanium or a durable plastic, such as polycarbonate or a liquid crystal polymer. In a first expression of one embodiment, pin 27 is partially coated with an elasto-meric material 30, such as silicon for that portion 29 of pin 27 that extends through waveguide 80 and uncoated for that portion of pin 27 that engages members 69 and 70. The silicone provides insulation from the vibrating blade throughout the length of hole 66. This enables high efficiency operation whereby minimal overheating is generated and maximum ultrasonic output power is available at the blade tip for cutting and coagulation. The lack of insulation allows pin 27 to be held firmly within handle assembly 68 due to the lack of insulation, which would provide deformation and movement if pin 27 were completely coated with an insulating material.

Referring now to FIGS. 8 and 9A-C a first expression of clamp member 56 has a shaped slot 57 for accepting one or more tissue pads. This configuration prevents mis-loading of the tissue pads and assures that the appropriate pad is loaded at the correct location within clamp member 56. For example clamp member 56 may comprise a T-shaped slot 57 to accept a T-shaped flange 55 of clamp pad 58. Two mechanical stops 59 and 59a, when depressed, engage the proximal end of clamp pad 58 to secure the clamp pad within clamp member 56. As would be appreciated by those skilled in the art, flanges and corresponding slots may have alternate shapes and sizes to secure the clamp pads to the clamp arm The illustrated flange configurations shown are exemplary only and accommodate the particular clamp pad material of one embodiment, but the particular size and shape of the flange may vary, including, but not limited to, flanges of the same size and shape. For unitary tissue pads, the flange may be of one configuration. Further, other tab stops are possible and may include any of the multiple methods of mechanically attaching the clamp pads to the clamp arm, such as rivets, glue, press fit or any other fastening means well know to the artisan.

Figure 10A:
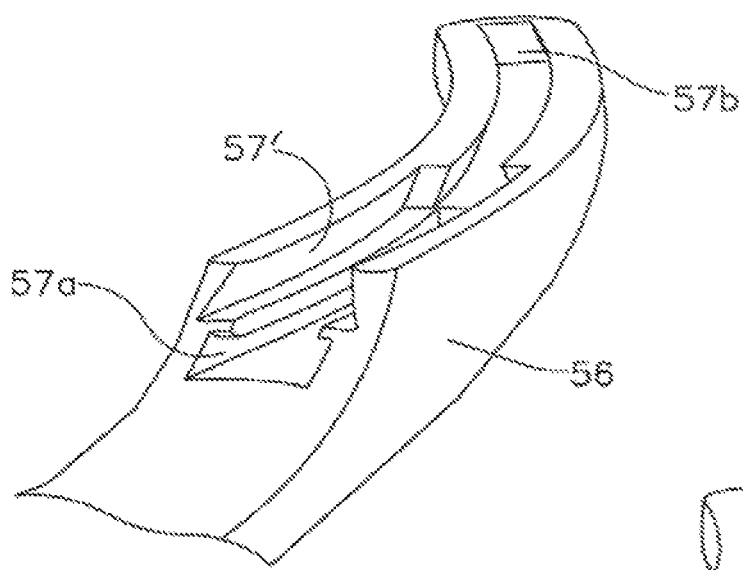
FIG. 10A is a perspective view of an alternate expression of the clamp member.
Figure 10B:
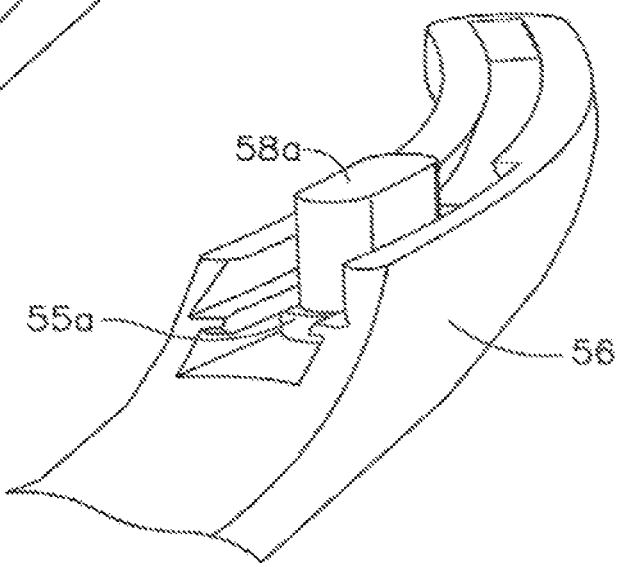
FIG. 10B is a perspective view of the clamp member of FIG. 10A and a first tissue pad.
Figure 10C:
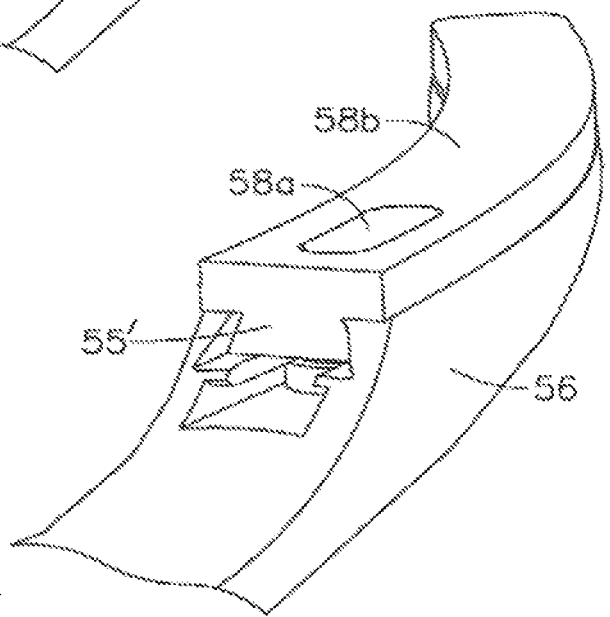
FIG. 10C is a perspective view of the clamp member of FIG. 10A and a first and second tissue pad.

Referring to FIGS. 10A-C, in a first expression of an alternate embodiment, clamp pad 58 consists of a first tissue pad 58b and a second pad portion 58a, which may be an insert within pad 58b. Tissue pad 58b may comprise a tissue engaging surface having saw tooth-like teeth and proximal portion 58a may have a smoother surface relative to pad 58b. The advantage of two separate components 58a and 58b is that each pad may be constructed from different materials. For example, having a two-piece tissue pad allows the use of a very lubricious material at the distal end that is not particularly resistant to high temperatures compared to a very high temperature material at the proximal end that is not particularly lubricious because the proximal end is an area of lower amplitude. Such a configuration matches the tissue pad materials to the amplitude of the blade 79.

In a second expression of an alternate embodiment of the present invention, clamp pad 58b is formed from TEFLON® or any other suitable low-friction material. Clamp pad 58a is formed from a base material and at least one filler material, which is a different material from the base material. The surface of proximal clamp pad 58a may be smoother than distal clamp pad 58b, or proximal clamp pad 58a may also have a similar type saw-tooth configuration.

Several benefits and advantages are obtained from one or more of the expressions of the invention. Having a tissue pad with a base material and at-least-one filler material allows the base material and the at-least-one filler material to be chosen with a different hardness, stiffness, lubricity, dynamic coefficient of friction, heat transfer coefficient, abradability, heat deflection temperature, glass transition temperature and/or melt temperature to improve the wearability of the tissue pad, which is important when high clamping forces are employed because tissue pads wear faster at higher clamping forces than at lower clamping forces. In experiments, a 15% graphite-filled polytetrafluoroethylene tissue pad showed substantially the same wear with a 7 pound clamping force as a 100% polytetrafluoroethylene tissue pad showed with a 1.5 pound clamping force. Having a flexible clamping arm and/or a flexible tissue pad should also improve the wearability of the tissue pad due to the ability of the flexible member to more evenly distribute the load across the entire surface of the tissue pad. Further benefits and expressions of this embodiment are disclosed in U.S. provisional patent application, Ser. No. 60/548,301, filed on Feb. 27, 2004 and commonly assigned to the assignee of the present application.

In a third expression of an alternate embodiment, a tissue pad with a base material and at least two filler materials allows the base material and the at-least-two filler materials to be chosen with a different hardness, stiffness, lubricity, dynamic coefficient of friction, heat transfer coefficient, abradability, heat deflection temperature, and/or melt temperature to improve the wearability of the tissue pad, which is important when high clamping forces are employed because tissue pads wear faster at higher clamping forces than at lower clamping forces. In experiments, a 15% graphite-filled, 30% PTFE-filled polyimide tissue pad showed substantially the same or better wear with a 4.5 pound clamping force as a 100% polytetrafluoroethylene tissue pad showed with a 1.5 pound clamping force. The advantage of a 15% graphite-filled, 30% PTFE-filled polyimide tissue pad is increased heat resistance, which improves the overall wear resistance of the tissue pad. This polyimide-composite clamp pad has a useful heat resistance up about 800° F. to about 1200° F., as compared to a useful heat resistance up to about 660° F. of a PTFE clamp pad. Alternatively, other materials are also useful for a portion of the tissue pad, such as ceramics, metals, glasses and graphite.

FIGS. 10A-C disclose a first expression of an embodiment of attaching a two part clamp pad 58a-b to a clamp member 56. In FIG. 10A, at least two slots 57a and 57b are shaped to accept two correspondingly shaped flanges 55a and 55'. In this example, T-slot 57a accepts a corresponding T-flange 55a of clamp pad 58a, and wedge-shaped slot 57' accepts a corresponding wedge-shaped flange 55' of clamp pad 58b.

Figure 11E:
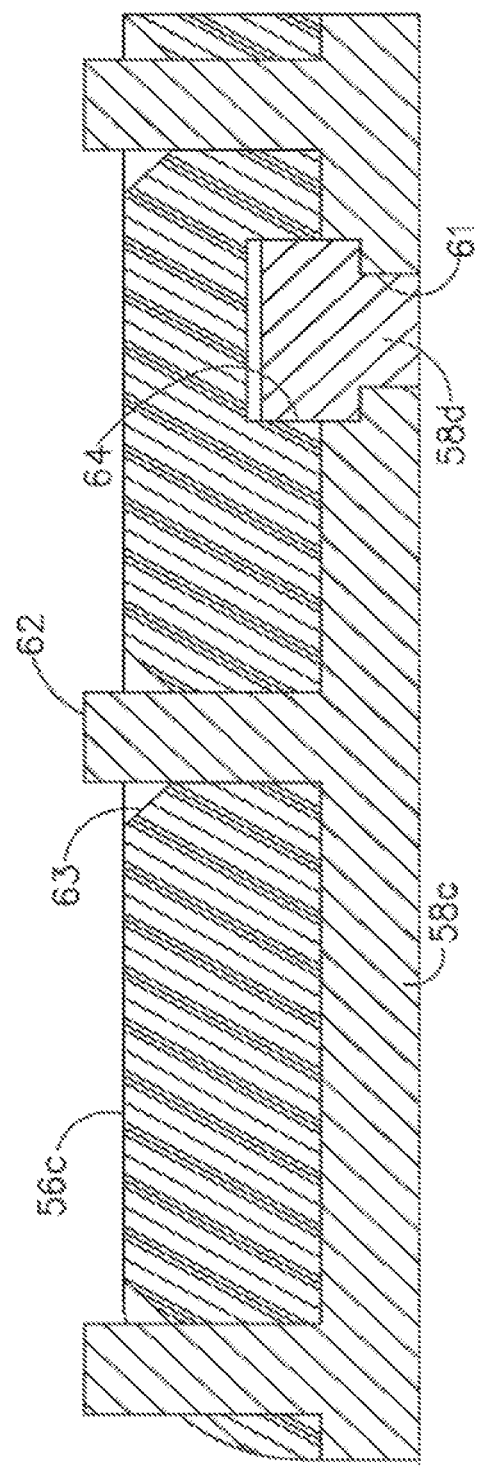
FIG. 11E is a cut-away view of an assembled clamp arm and tissue pad assembly of FIGS. 11A-D.

FIGS. 11A-E illustrate a second expression of attaching a clamp pad 58c to a clamp arm 56c. Clamp pad 58c comprises one or more protrusions 62 for insertion into one or more corresponding apertures 63 in clamp arm 56c. If a second or more clamp pad(s) 58d is also used in accordance with the previous discussion, then clamp pad 58c further comprises corresponding aperture 61 for accepting one or more clamp pad(s) 58d. Clamp arm 56c has corresponding aperture(s) 63 for accepting protrusions 62, as well as a corresponding cavity 64 for accepting the one or more clamp pad 58d. FIG. 11E illustrates the components assembled together prior to staking. Clamp pad 58d fits inside the aperture 61 and cavity 64, and pad 58c is aligned with clamp arm 56c so that protrusions 62 align with chamfered aperture 63. Protrusions 62 have additional height beyond the top surface of clamp arm 56c to provide additional material to fill the chamfered volume during staking. Heat is applied to protrusions 62 above the clamp arm 56c; the protrusions deform and take the shape of the chamfered volume.

Figure 12A:
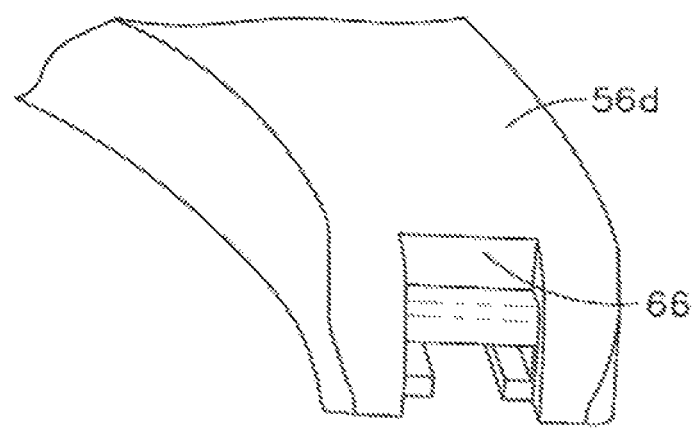
FIG. 12A is a perspective view of an alternate embodiment of a clamp arm having a distal connection point.
Figure 12B:
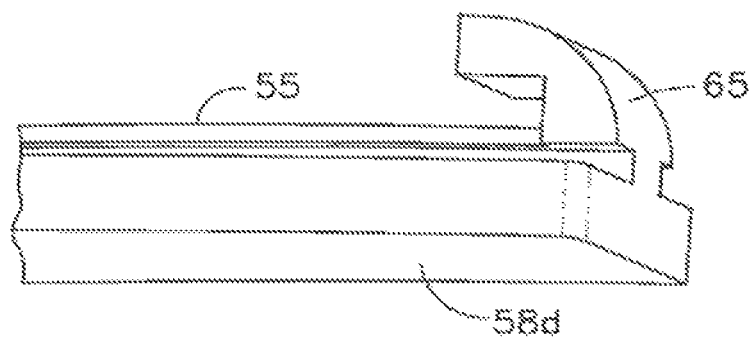
FIG. 12B is a perspective view of an alternate embodiment of a tissue pad having a distal connection member.
Figure 12C:
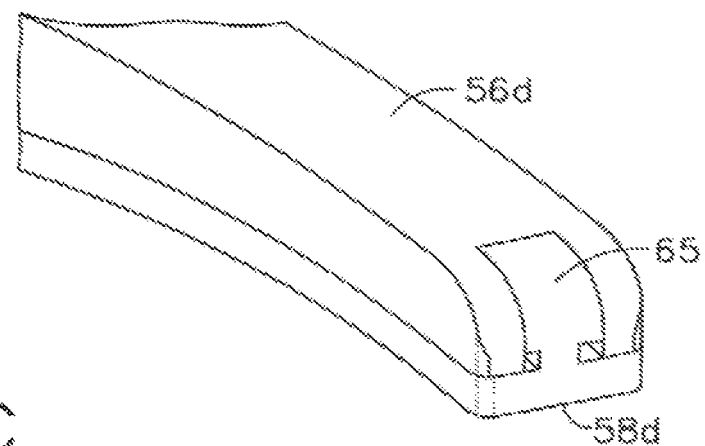
FIG. 12C is a perspective view of an assembled clamp arm and tissue pad of FIGS. 12A-B.

FIGS. 12A-C illustrate a third expression of attaching a clamp pad 58d to a clamp arm 56d. In addition to a T-shaped flange 55, clamp pad 58d further comprises a hook-like protrusion or clip 65 for attaching to a corresponding opening 66 at the distal tip of clamp arm 56d. In this expression, the distal tip of clamp arm 56d is open and the clamp pad 58d is inserted from the distal to proximal direction until the hook clip engages opening 66. Hook clip 65 may be biased closed so when clip 65 engages opening 66, clip 65 applies compressive forces against opening 66.

A first expression for a method for inserting a clamp pad on a clamp arm includes a) inserting a first clamp pad having a first width dimension greater than a second width dimension and having a first-shaped flange into a clamp arm having a slot that accepts the first-shaped flange; and b) engaging a pad stop to secure the clamp pad within the clamp arm In a second expression of the method, the clamp pad consists of a second clamp pad fabricated from a base material and at least one filler material, which is a different material from the base material. The second clamp pad may have a second-shaped flange for engaging a second-shaped slot on the clamp arm The tissue surfaces of the clamp pads may be smooth or have tissue gripping features, such as a saw-tooth configuration.

A first expression for a method for replacing clamp pads would include the steps of: a) disengaging a pad stop; b) removing a first clamp pad from the clamp arm; c) removing a second clamp pad from the clamp arm, wherein at least one of the first or second clamp pads has a first width dimension greater than a second width dimension; d) inserting third and fourth clamp pads into the clamp arm wherein at least one of the third or fourth clamp pads has a first width dimension greater than a second width dimension; and e) engaging a pad stop to secure the third and fourth clamp pads within the clamp arm In a second expression of this method one of the third and fourth clamp pads may be fabricated from a polymeric material such as TEFLON, and the other clamp pad may be fabricated from a base material and at least one filler material, which is a different material from the base material. The tissue surfaces of the clamp pads may be smooth or have tissue gripping features, such as a saw-tooth configuration.

Figure 13:
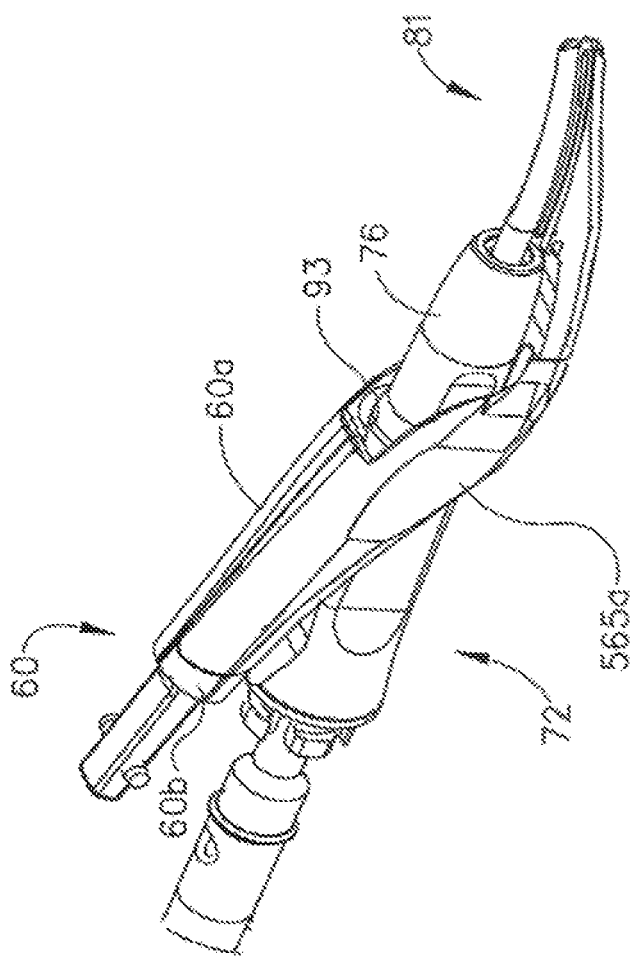
FIG. 13 is a partial view of the distal end of the ultrasonic instrument in accordance with the present invention.
Figure 14:
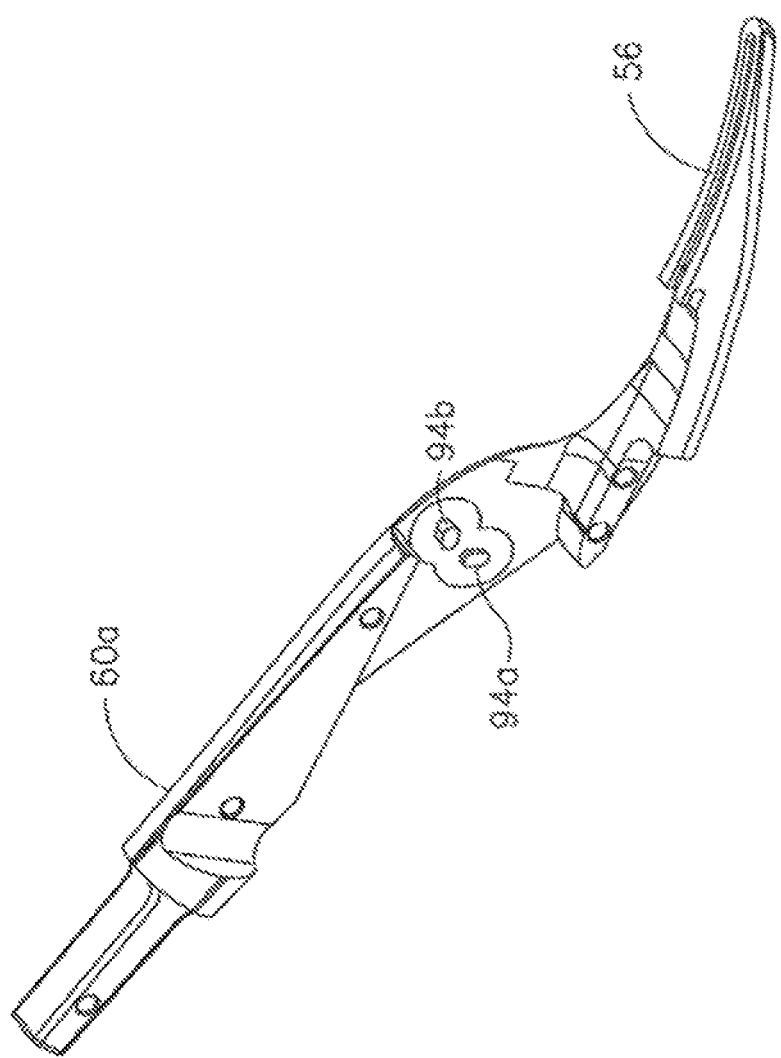
FIG. 14 is an exploded elevation view of one part of the clamp arm and clamp member and cam members.
Figure 15:
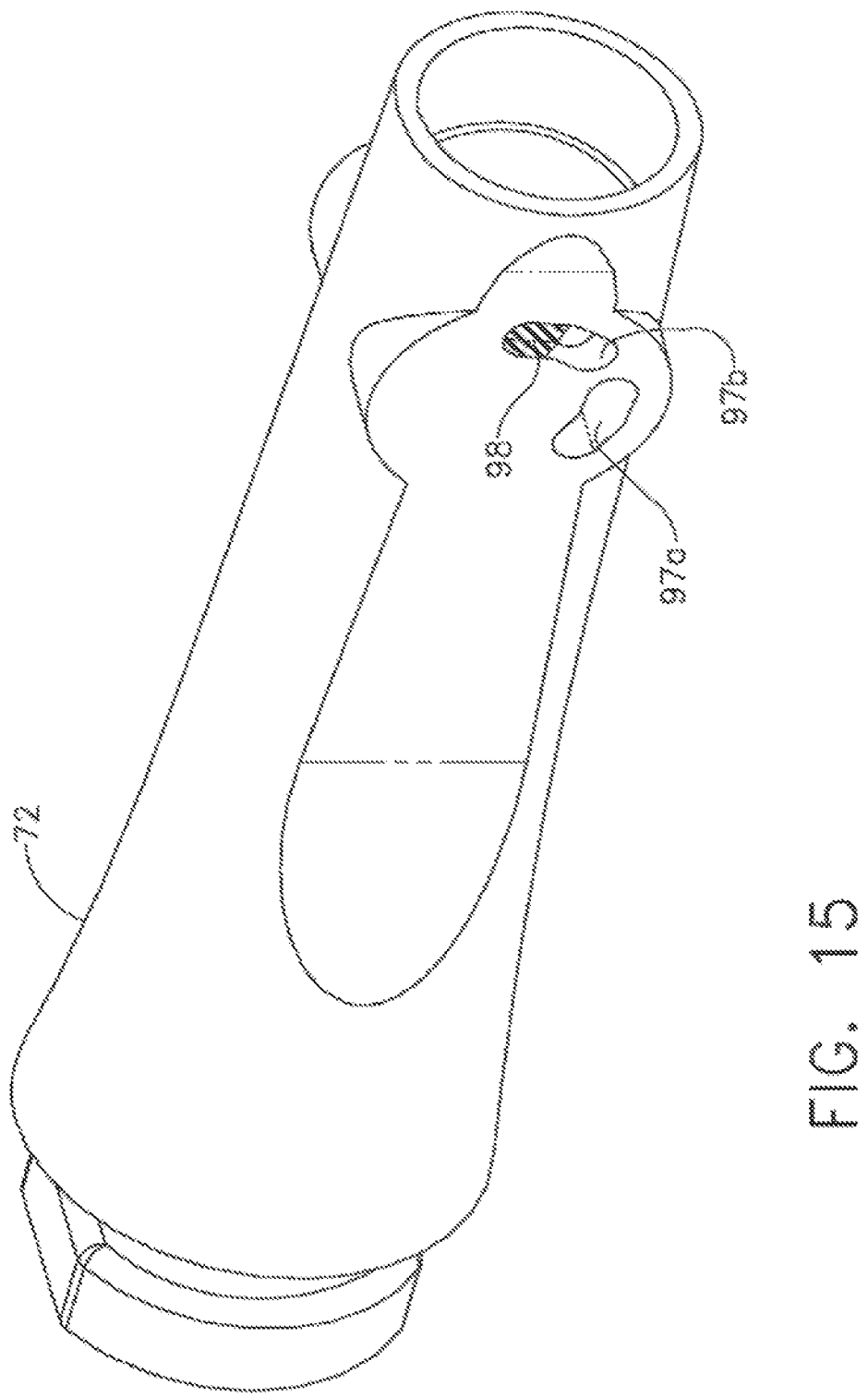
FIG. 15 is an exploded view of the outer shroud and cam slots.

Referring to FIGS. 13-15, a clamp arm 60 is configured for use with the present ultrasonic surgical instrument 100 and for cooperative action with blade 79 and clamp member 56. The clamp arm 60 is rotatably mounted to the distal end of outer shroud 72, detailed below, and connectably attaches at the distal end of thumb ring or actuation member 34. Clamp pad 58 mounts on the clamp member 56 for cooperation with blade 79, with rotational movement of the clamp arm 60 positioning the clamp pad in substantially parallel relationship to, and in contact with, blade 79, thereby defining a tissue treatment region. By this construction, tissue is grasped between clamp pad 58 and blade 79. Pivotal movement of the clamp member 56 with respect to blade 79 is affected by the provision of a pair of camming members on the clamp arm 60 that interface with the outer shroud 72. The outer shroud 72 is grounded to handle 68.

A first expression of clamp arm 60 comprises jaw-carrying member 60a and mating member 60b. Jaw-carrying member 60a includes two camming members 94a and 94b for mating with two corresponding camming slots 95a and 95b located outer shroud 72. Mating member 60b includes two camming members 96a and 96b for mating with two corresponding camming slots 97a and 97b located outer shroud 72. Corresponding camming members 94a/94b and 96a/96b (and corresponding camming slots 95a/95b and 97a/97b) may align along common axes perpendicular to the longitudinal axis of waveguide 80 or camming members may be offset to facilitate the assembly process. Members 60a and 60b fixedly attach to each other as shown in FIG. 13 to form clamp arm 60 via press fit or snap fit. Other attaching methods are available as is known to those skilled in the art, such as welding, glue, screwing, etc. Once assembled, clamp arm 60 defines an opening 93 for receiving outer shroud 72 and the interlocking of the respective cam members and cam slots. Alternatively, members 60a and 60b may be assembly around outer shroud 72 and all three elements mated together in one operation. One benefit of the cam open and closure mechanism is that it can provide both a rotational motion and linear motion of the clamp arm 60 and clamp member 56 thereby providing better control of the pressure profile between clamp pad 58 and blade 79.

In a second expression of clamp arm 60, the camming members may be replaced with spherical elements that interface with cam slots. Alternatively camming members may be replaced with spherical depressions for receiving ball bearings that interface with the cam slots. Other camming mechanism would be useful as is well known to the skilled artisian.

With solid camming members and corresponding slots, the force delivered between the clamp pad 58 and blade 79 is directly related to the force that the user applies at the thumb ring 35 and finger ring 36. In a third expression of clamp arm 60, a force limiting element 98, such as an elastomer or coil or leaf spring, may be inserted within one or more cam slots and provide a force limit to the coaptation force seen at the end effector 81. Preferably, the spring constant of an elastomer or spring ranges from 10-500 lb./in.

Outer shroud 72, distal shroud 76 and clamp arm 60 may be constructed from any number of biocompatible materials, such as titanium, stainless steel or plastics. Preferably, however, these elements are constructed of either 7075 or 6061 T6 aluminum. The aluminum provides a large benefit in terms of heat dissipation. Devices of the prior art have sheaths and clamp arms made of stainless steel. Typical values for thermal conductivity for aluminum are around 250 W/m K. The values for stainless steel are around 16 W/m K. Thus, aluminum has approximately 15 times greater capability to transmit heat through the same amount of volume.

The inventors have found through testing of similar inputs (clamp force and blade displacement), the present invention operates approximately 150° F. lower in temperature than instruments of the prior art. The aluminum components more effectively draw the heat away from the pad and the blade, thus keeping the end effector cooler than other prior art instruments.

Referring now to FIGS. 1, 2 and 16A-G housing 68 includes a proximal end, a distal end, and a cavity 59 extending longitudinally therein. Cavity 59 is configured to accept a switch assembly 300 and the transducer assembly 50.

In one expression of the current embodiment, the distal end of transducer 50 threadedly attaches to the proximal end of transmission rod 80. The distal end of transducer 50 also interfaces with switch assembly 300 to provide the surgeon with finger-activated controls on surgical instrument 19.

Transducer 50 includes a first conductive ring 400 and a second conductive ring 410 which are securely disposed within the transducer body 50 as is described in co-pending application Ser. No. 12/248,262, now U.S. Pat. No. 8,328,834.

Switch assembly 300 comprises a pushbutton assembly 310, a flex circuit assembly 330, a switch housing 350, a first pin conductor 360 and a second pin conductor 370. Switch housing 350 is saddle-shaped and is supported within handle assembly 68 by way of corresponding supporting mounts on switch housing 350 and housing portions 69 and 70. Housing 350 defines a first receiving area 353 for a dome switch, and a second receiving area 351 for a dome switch.

Figure 16A:
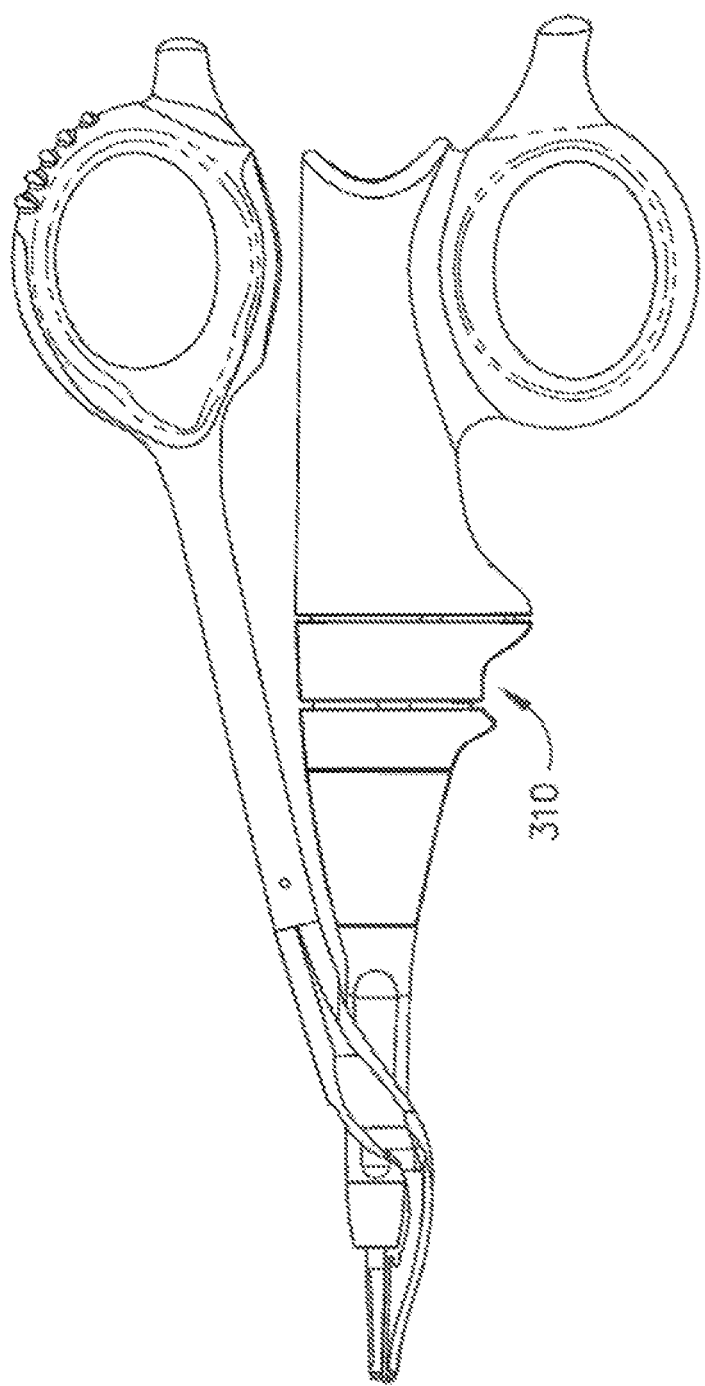
FIG. 16A is an elevation view of an ultrasonic instrument and pushbutton assembly in accordance with the present invention.
Figure 16B:
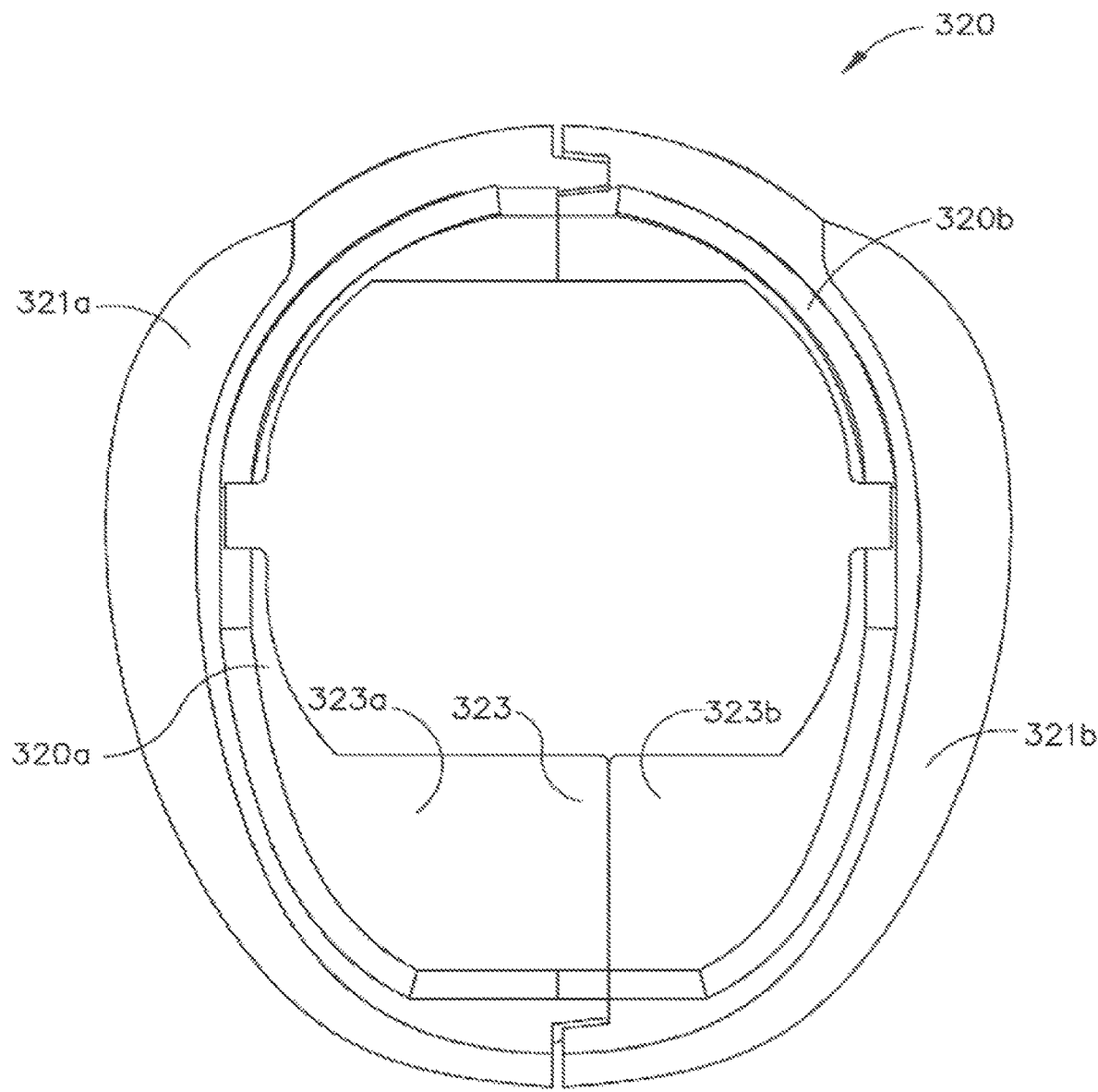
FIG. 16B is an elevation view of the two piece assembly of a push button in accordance with the present invention.
Figure 16D:
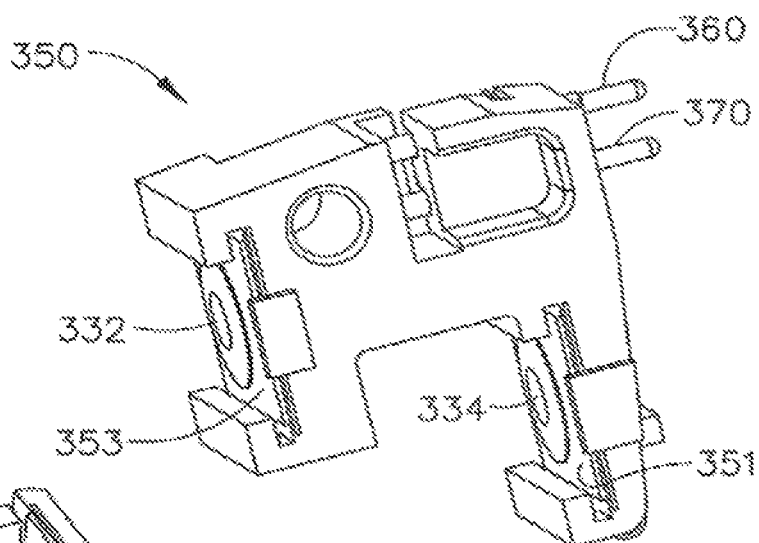
FIG. 16D is a perspective elevation view of a switch housing in accordance with the present invention.
Figure 16E:
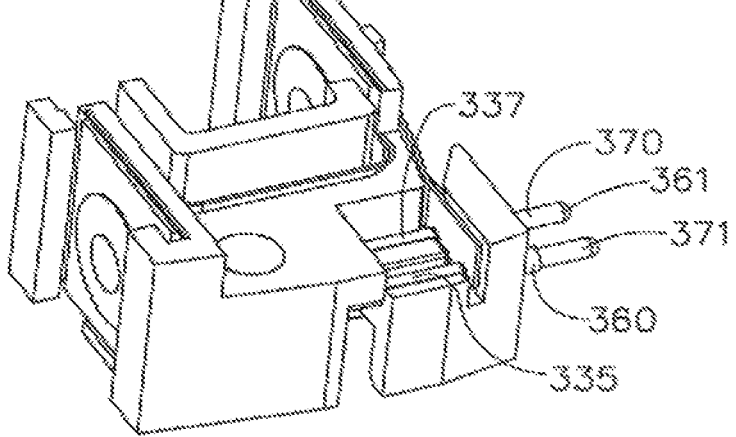
FIG. 16E is an alternate view of the switch housing of FIG. 16D.
Figure 16F:
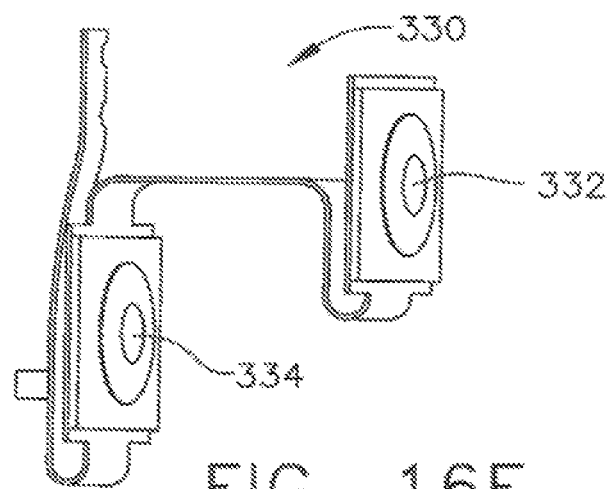
FIG. 16F is a view of a flex circuit in accordance with the present invention.

With particular reference now to FIGS. 16D and E, pins 360 and 370 are electrically connected to dome switch 332 and 334 via conductors 337 and 335, respectively, at one end and to the distal end of transducer 50 at a second end. Pins 360 and 370 each have a spring-loaded tip 361 and 371 that interface with transducer 50 as shown in FIG. 16C. Each end 361 and 371 have a 0.050 inch working travel to allow for manufacturing tolerances associated with the stackup of the assembled parts. Slidably attached to housing 68 are two triggers 320 and 322, each comprising first and second halves 320a, 320b and 322a, 322b, respectively. Shown in FIG. 16B is trigger 320, which comprises ridges 321a and band contact surface 323 (made up of mating surfaces 323a and 323b). When assembled, triggers 320 and 322 slidably attach to housing 68 and contact surfaces 323 and 325 mechanically engage dome switches 332 and 334, respectively. Ridges 321 and 326 provide interface between the user and triggers 320 and 322. Ridges 321 and 326 are designed to provide as much surface area for the user to depress in order to activate the instrument.

In a second expression of switch assembly 300 elastomeric connectors having copper traces etched onto the elastomer press fit into switch housing 350 to provide the electrical interconnect between transducer 50 and flex circuit 330. One end of the elastomer connectors electrically engage dome switches 332 and 334 via conductors 337 and 335. The other end of the elastomer connectors slidably interface with conductors 400 and 410 of transducer 50. Compression of the elastomer connectors allow a working travel of up to 20% of the total height of the elastomer connectors to allow for manufacturing tolerances associated with the stackup of the assembled parts.

A flex circuit 330 provides for the electro-mechanical interface between pushbuttons 321 and 322 and the generator 30 via transducer 50. Flex circuit comprises two dome switches 332 and 334 that are mechanically actuated by depressing pushbuttons 321 or 322 axially in the x direction. Dome switches 332 and 334 are electrical contact switches, that when depressed provide an electrical signal to generator 30 as shown by the electrical wiring schematic of FIG. 16G. Flex circuit 330 also comprises two diodes within a diode package 336 and conductors, 335 and 337 as is known to those in the art, that connect to pins 360 and 370, respectively, which in turn provide electrical contact to ring conductors 400 and 410, which in turn are connected to conductors in cable 22 that connect to generator 30.

Flex circuit 330 generally sits within a channel 352 of switch assembly 350 so that dome switches 332 and 334 interface with the corresponding backing surfaces 351 and 353. Backing surfaces provide a firm support for the dome switches during operation, discussed below. Dome switches 332 and 334 may be fixedly attached to backing surfaces 351 and 353 by any convenient method, such as, an adhesive.

As is readily apparent, by depressing pushbuttons 321 and 322 the corresponding contact surfaces 323 and 324 depress against corresponding dome switches 332 and 334 to activate the circuit illustrated in FIG. 16G. When the surgeon depresses 321 pushbutton, the generator will respond with a certain energy level, such as a maximum ("max") power setting; when the surgeon depresses pushbutton 322, the generator will respond with a certain energy level, such as a minimum ("min") power setting, which conforms to accepted industry practice for pushbutton location and the corresponding power setting.

Figure 17A:
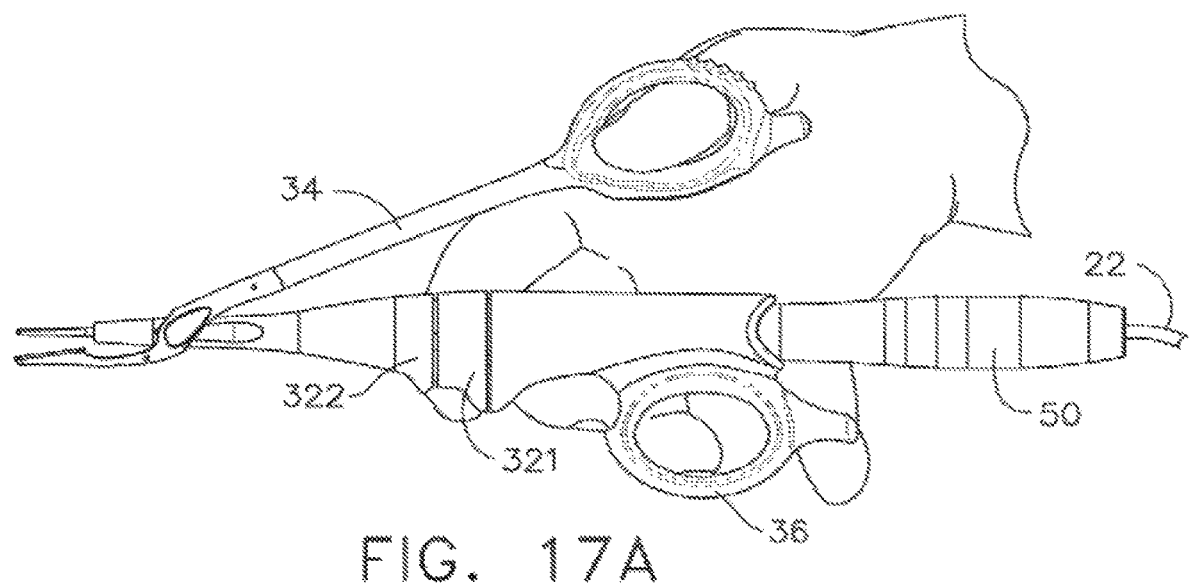
FIG. 17A is an elevation view of an ultrasonic instrument in accordance with the present invention as may be grasped by a user.
Figure 17B:
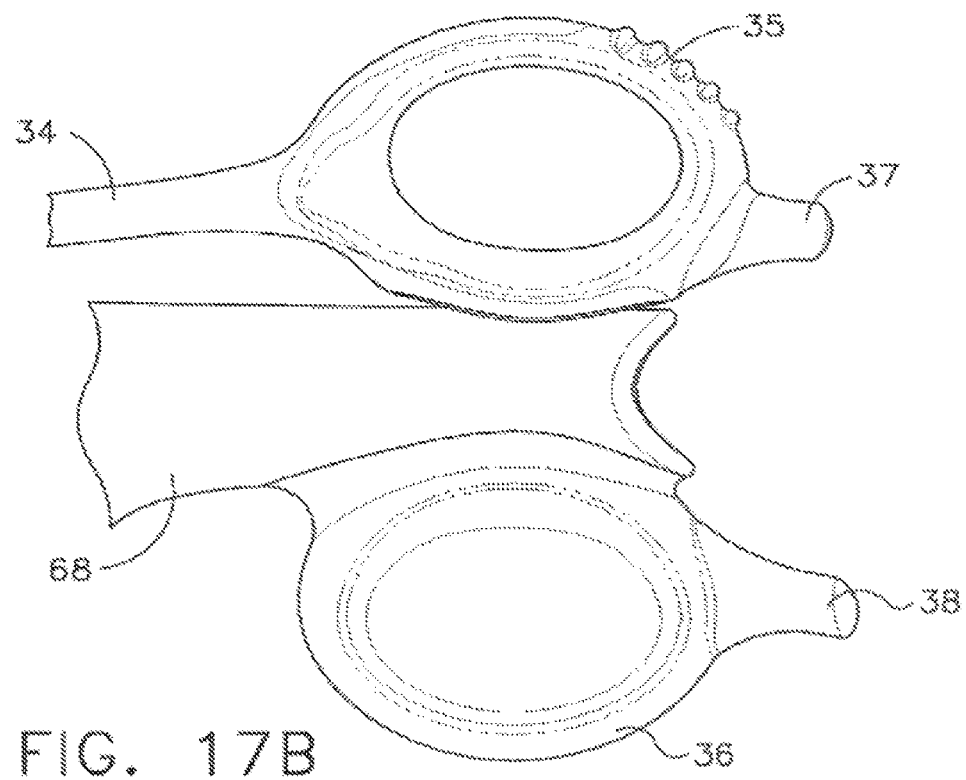
FIG. 17B is an exploded view of the finger and thumb interface of a ultrasonic instrument in accordance with the present invention.

Referring now to FIGS. 17 A-B, the pushbutton axial actuation reduces stress on the surgeon's fingers and allows the fingers to actuate force in a more ergonomic position preventing stresses at the hands and wrists. The switch movement also allows comfortable button activation in less than optimal hand positions, which surgeons often encounter throughout a typical procedure.

At the proximal end of each access ring 35 and 36 are protrusions 37 and 38, respectively, that allow the surgeon to rest his or her pinky finger for added control and comfort. This also allows the surgeon to use the pinky when clamping on tissue, thereby reducing the force on the other fingers.

Each access ring 35 and 36 includes a soft-touch surface on the interior and exterior surfaces whether by inserting fingers into the access rings or palming the access rings. This feature allows a greater number of hand sizes to comfortably use the device.

Figure 18:
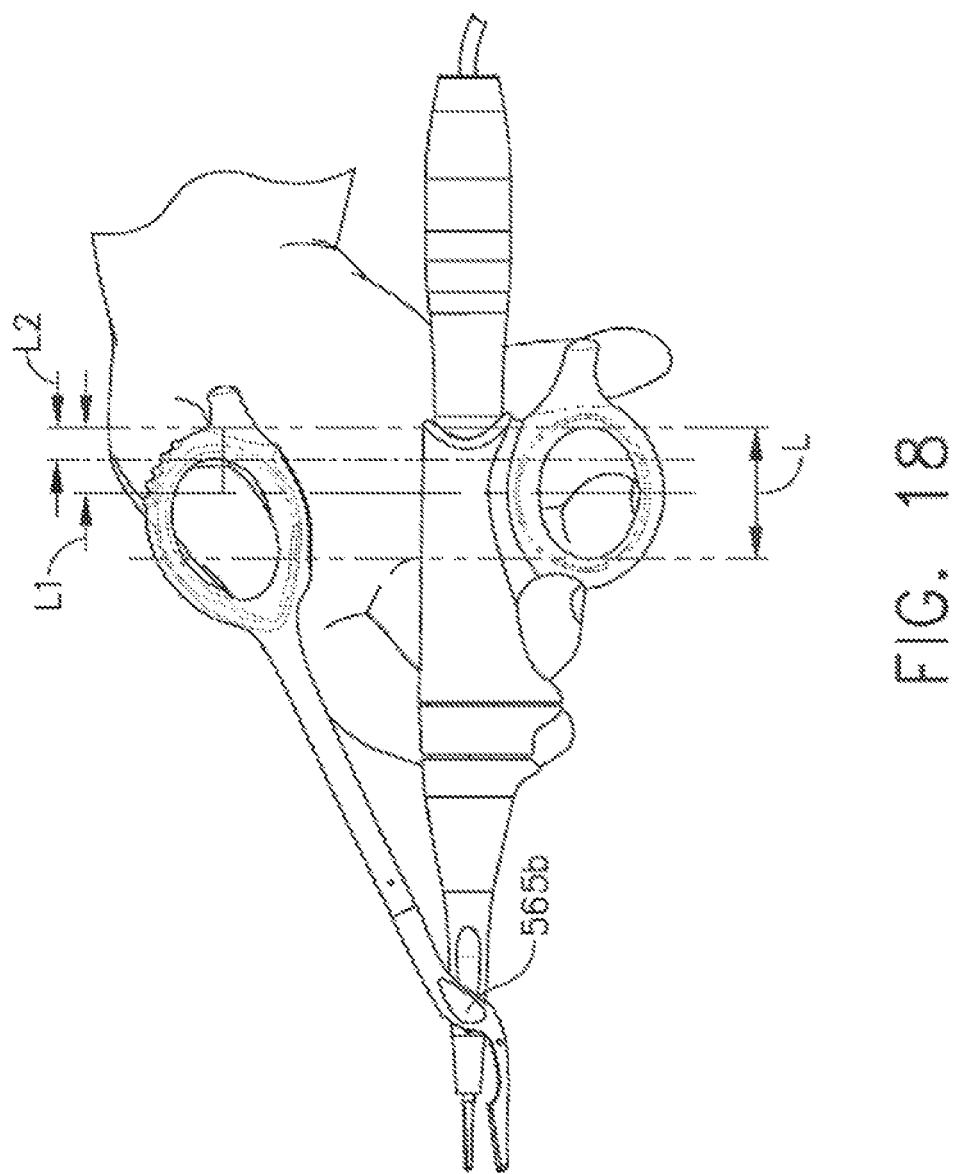
FIG. 18 is an elevation view of an ultrasonic instrument in accordance with the present invention as may be grasped by a user and defining a center of gravity.
Figure 19A:
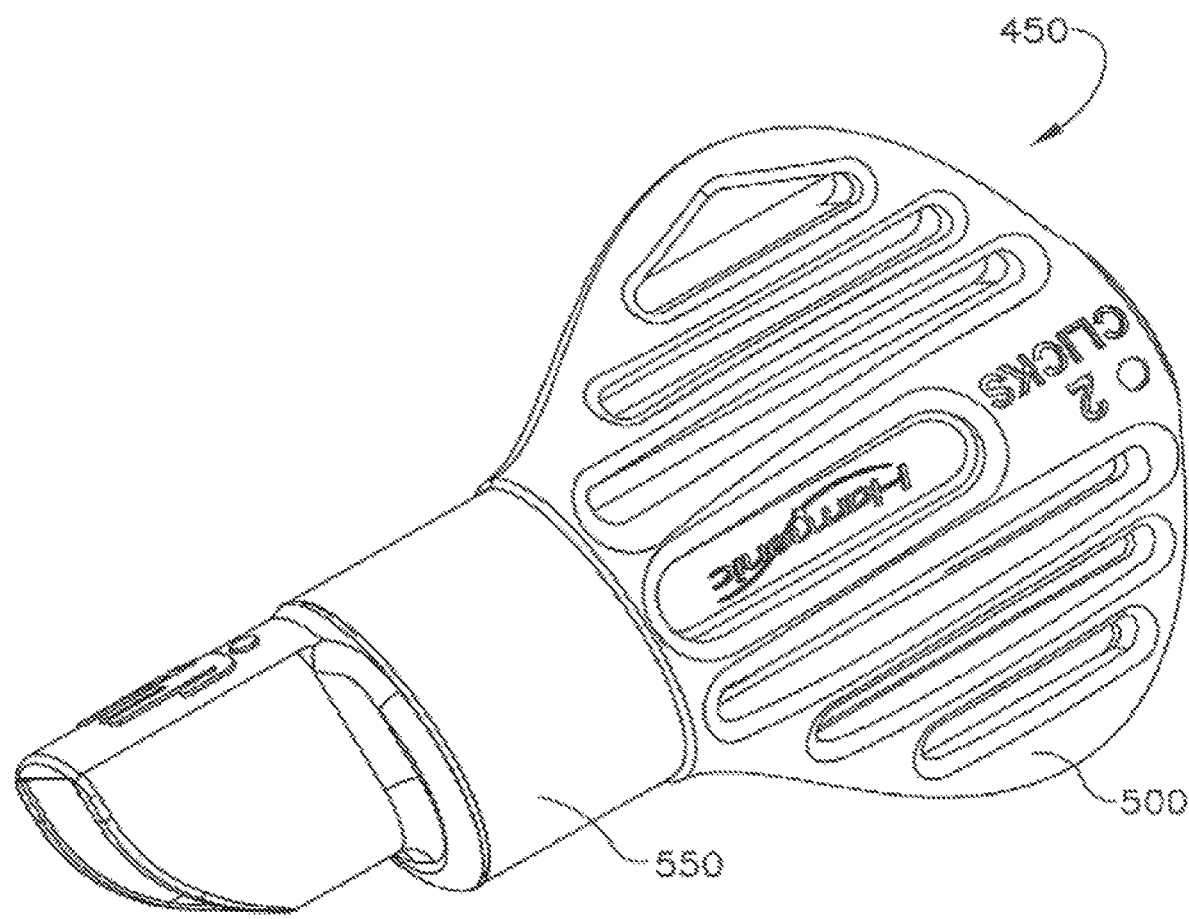
FIG. 19A is a perspective view of a two-piece torque wrench in accordance with the present invention.
Figure 19B:
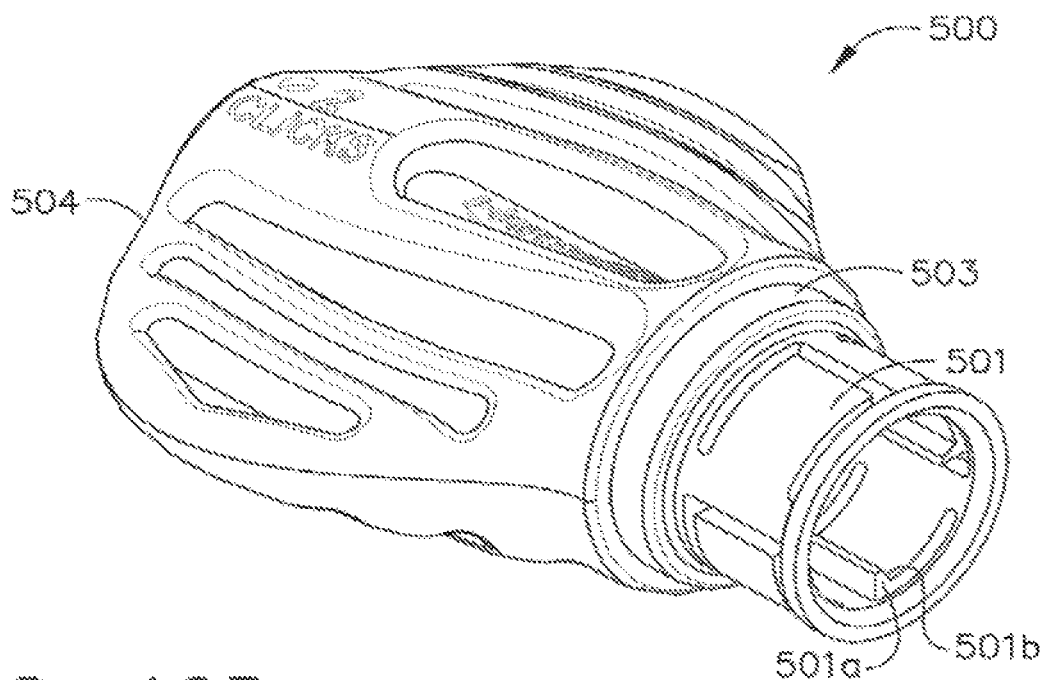
FIG. 19B is a perspective view of a hand wrench in accordance with the present invention.
Figure 19C:
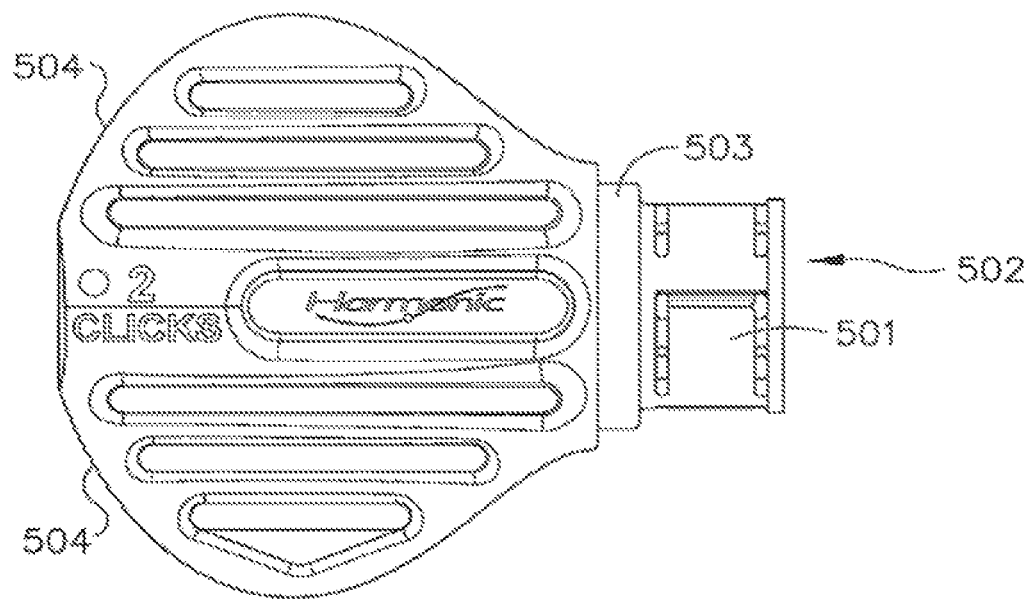
FIG. 19C is an elevation view of the hand wrench of FIG. 19B.
Figure 19D:
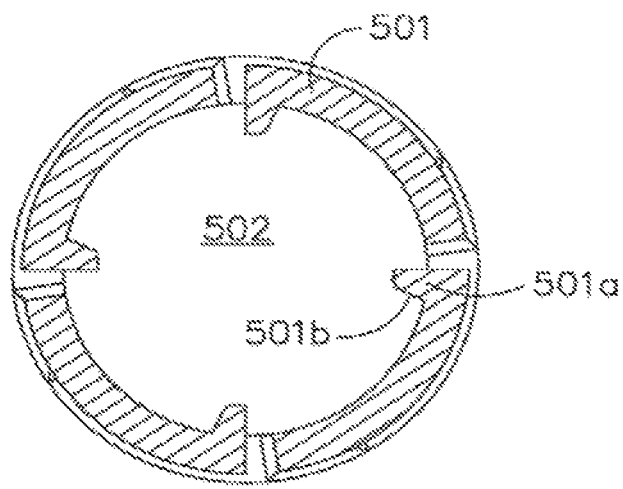
FIG. 19D is a cross sectional end view of the distal end of a hand wrench depicting cantilever arm and teeth geometry.
Figure 19E:
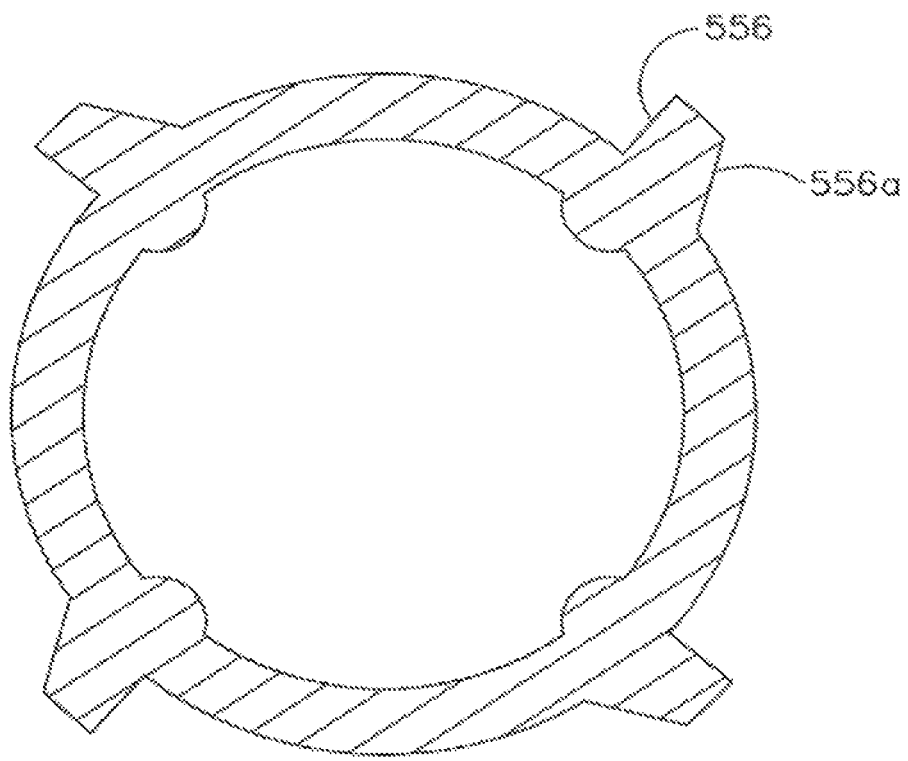
FIG. 19E is a cross sectional view of an adaptor depicting spline gear geometry.
Figure 19F:
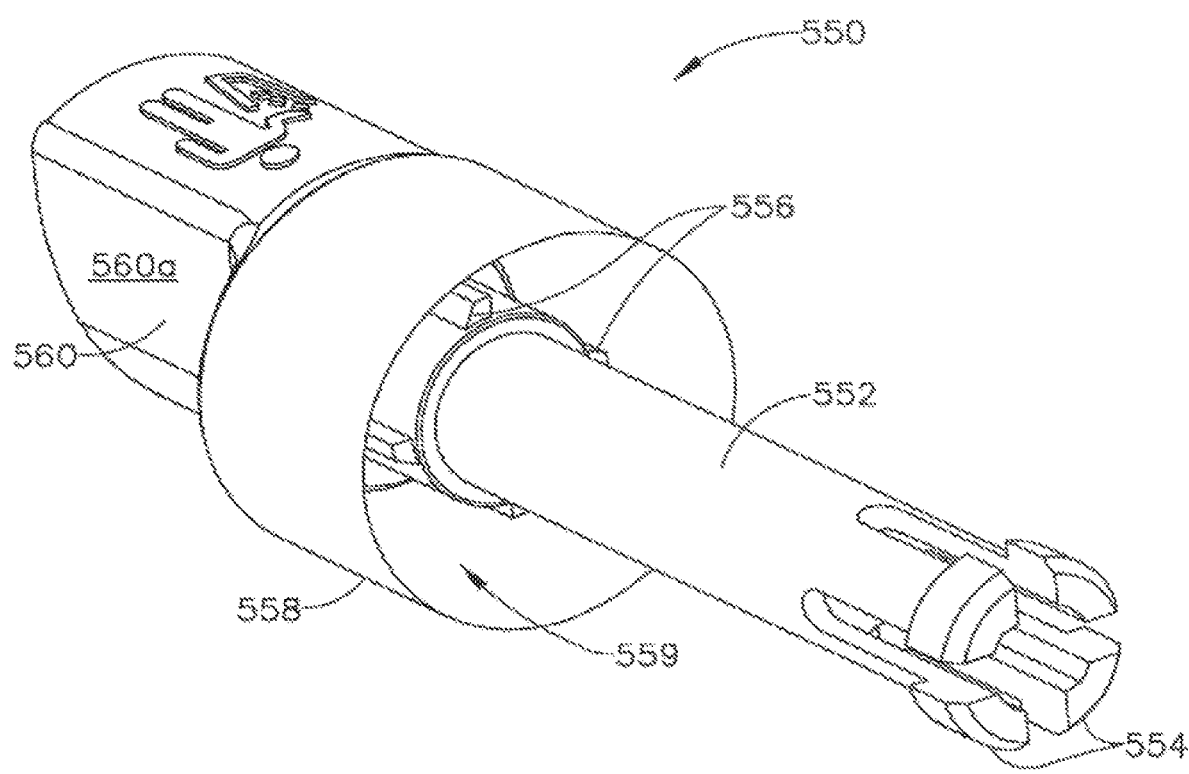
FIG. 19F is a perspective view of an adaptor for use with a hand wrench in accordance with the present invention.
Figure 19G:
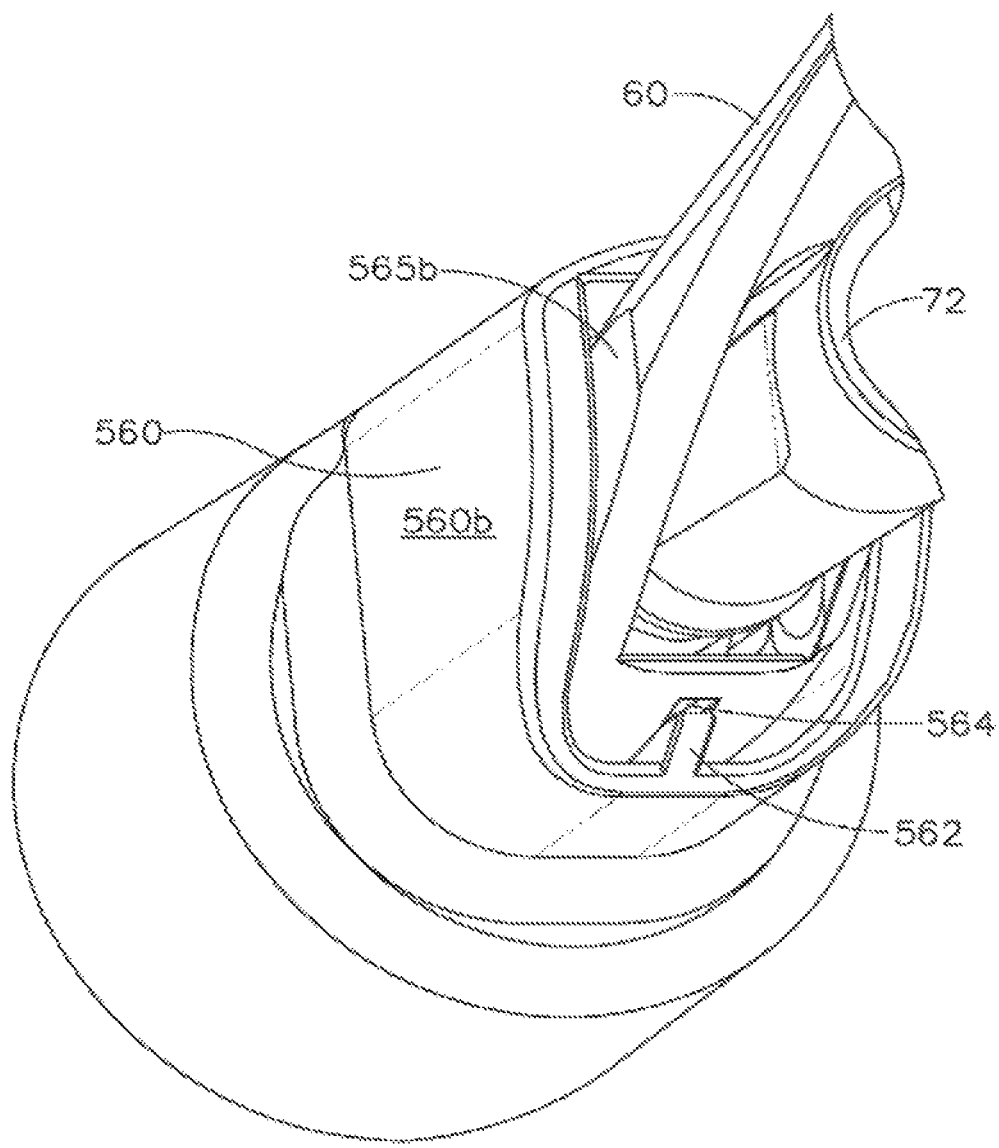
FIG. 19G is a partial perspective view of a hand wrench interfacing with an ultrasonic instrument in accordance with the present invention.

Referring to FIG. 18, access rings 35 and 36 define a length L. Preferably, the center of gravity of the surgical instrument 100 in combination with the transducer 50 is positioned within length L, more preferably within length L1, and most preferably within length L2. This position of the center of gravity allows the instrument to balance within the surgeon's hand to provide more precise control of the instrument and eliminate hand fatigue during procedures.

Referring now to FIGS. 18 and 19A-E, a two-piece torque wrench 450 is shown. The torque wrench includes a hand wrench 500 and an adaptor 550. In one embodiment, hand wrench 500 is provided with cantilever arms 501 disposed in an annular fashion about the centerline of hand wrench 500. Cantilever arms 501 include teeth 501a disposed, in one embodiment, in an inward perpendicular fashion in relation to cantilever arms 501. Teeth 501a, in one embodiment of the current invention, are disposed with a cam ramp 501b at a 25° angle with respect to the perpendicular angle between arm 501 and teeth 501a. Lumen 502 extends the entire length of hand wrench 500 for accepting adaptor 550.

Adaptor 550 has a longitudinal shaft 552 with cantilevered tabs 554 at its distal end. At the proximal end of shaft 552 are spline gears 556 projecting in a perpendicular fashion along the outer circumference of shaft 552. Spline gears 556 include cam ramps 556a disposed at an angle from about 23° to about 28° with respect to the perpendicular angle between the outer circumference of shaft 552 and spline gears 556. Shaft 552 further defines a lateral opening (not shown) proximal to spline gears 556 for accepting curved blade 79, discussed below. Adaptor further includes an interface 560 rigidly connected to shaft 552 and defining an opening for rigidly engaging the distal end of instrument 19. Optionally, a skirt 558 surrounds spline gears 556 to prevent glove snags due to moving parts and forms a cavity 559.

In assembly, torque wrench opening 502 is aligned with shaft 552 and guided along substantially the entire length of shaft 552 until the tabs 554 flex inward and capture shoulder 505 (not shown) at the distal end of hand wrench 500. Hand wrench lip 503 engages the distal end of optional skirt 558 allowing cantilever teeth 501a to slidably engage spline gears 556. Cam ramp 501b slidably engages retainer cam ramps 29b. The torque wrench assembly 450 slidably engages the distal end of instrument 19 and is held rigidly in place. Flat surfaces 560b and 560a of interface 560 mate with flat surfaces 565b (FIG. 18) and 565a (not shown) at the distal end of activation member 34 (clamp arm 60) and rail 562 slidably engaging slot 564 on clamp arm 60 and distra shroud 76 and outer shroud 72 all provide structural support to maintain adapter 550 firmly engaged with instrument 19.

Clockwise annular motion or torque is imparted to hand wrench 500 through paddles 504. The torque is transmitted through arms 501 and teeth 501a to gears 556, which in turn transmit the torque to the waveguide 80 via clamp arm assembly 60 via outer shroud 72 via insulated pin 27. When a user imparts 5-12 lbs. of torque, the ramps 501b and 556 cause the arms 501 to move or flex away from the centerline of wrench 500 ensuring that the user does not over-tighten the waveguide 80 onto transducer 50. When a counterclockwise torque is applied to wrench 500 via paddles 504, the perpendicular flat sides of teeth 501a and 556 abut allowing a user to impart a torque to the interface between the waveguide 80 and transducer 50 in proportion to the force applied to the paddles facilitating removal of the instrument 100 from the transducer 50. The torque wrench 450 may be constructed from a durable plastic, such as polycarbonate or a liquid crystal polymer. It is also contemplated that the wrench 450 may alternatively be made from a variety of materials including other plastics, ceramics or metals.

In another embodiment (not shown), the paddles and cantilever arm assembly may be separate components attached by mechanical means or chemical means such as adhesives or glue.

Preferably, the ultrasonic clamp coagulator apparatus 19 described above will be processed before surgery. First, a new or used ultrasonic clamp coagulator apparatus is obtained and if necessary cleaned. The ultrasonic clamp coagulator apparatus can then be sterilized. In one sterilization technique the ultrasonic clamp coagulator apparatus is placed in a closed and sealed container, such as a plastic or TYVEK bag. Optionally, the ultrasonic clamp coagulator apparatus can be bundled in the container as a kit with other components, including a torque wrench 450. The container and ultrasonic clamp coagulator apparatus, as well as any other components, are then placed in a field of radiation that can penetrate the container, such as gamma radiation, x-rays, or high-energy electrons. The radiation kills bacteria on the ultrasonic clamp coagulator apparatus and in the container. The sterilized ultrasonic clamp coagulator apparatus can then be stored in the sterile container. The sealed container keeps the ultrasonic clamp coagulator apparatus sterile until it is opened in the medical facility.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. An ultrasonic surgical system, comprising:
 a surgical instrument, comprising:
  a handle assembly, comprising:
   a first finger grip;
   an ultrasonic blade; and
   a waveguide extending proximally from the ultrasonic blade; and
  a body member pivotably coupled to the handle assembly, wherein the body member comprises:
   a second finger grip;
   a clamp arm movable relative to the ultrasonic blade to capture tissue therebetween;
   a first body surface defined on a first side of the body member; and
   a second body surface defined on a second side of the body member; and
 a wrench assembly, comprising:
  a wrench; and
  an adapter operably coupled to the wrench, wherein the adapter comprises:
   a first wrench surface configured to engage the first body surface; and
   a second wrench surface configured to engage the second body surface.

2. The ultrasonic surgical system of claim 1, wherein the adapter further comprises a rail, and wherein the clamp arm defines a slot configured to receive the rail.

3. The ultrasonic surgical system of claim 1, wherein the adapter defines an opening configured to receive the ultrasonic blade.

4. The ultrasonic surgical system of claim 1, wherein the wrench is configured to rotate relative to the adapter based on a threshold force applied to the wrench being reached or exceeded.

5. The ultrasonic surgical system of claim 1, wherein rotation of the wrench assembly is configured to impart a torque to the waveguide.

6. The ultrasonic surgical system of claim 1, wherein the handle assembly defines a cavity configured to removably receive a transducer assembly therein.

7. A wrench assembly for use with a surgical instrument comprising a handle assembly and a body member pivotally coupled to the handle assembly, wherein the handle assembly comprises a first finger ring, an ultrasonic blade, and a waveguide extending from the ultrasonic blade, wherein the body member comprises a second finger ring, a clamp arm movable relative to the ultrasonic blade to capture tissue therebetween, a first body surface defined on a first side of the body member, and a second body surface defined on a second side of the body member, wherein the wrench assembly comprises:
a wrench defining a longitudinal axis, wherein the wrench comprises:
an arm; and
a tooth extending from the arm toward the longitudinal axis; and
an adapter operably coupled to the wrench, wherein the adapter comprises:
a first wrench surface configured to engage the first body surface;
a second wrench surface configured to engage the second body surface;
a shaft; and
a spline gear extending from the shaft, wherein the tooth is configured to engage the spline gear based on rotation of the wrench, and wherein the arm is configured to flex away from the longitudinal axis based on a threshold force being applied to the wrench;
wherein the wrench comprises a plurality of arms comprising the arm, and wherein the plurality of arms extend circumferentially around the longitudinal axis.

8. The wrench assembly of claim 7, wherein the adapter further comprises a rail configured to be received in a slot of the clamp arm.

9. The wrench assembly of claim 7, wherein the adapter defines an opening configured to receive the ultrasonic blade.

10. The wrench assembly of claim 7, wherein the wrench is configured to rotate relative to the adapter based on the threshold force being reached or exceeded.

11. The wrench assembly of claim 7, wherein the first wrench surface comprises a substantially flat surface, and where the second wrench surface comprises a substantially flat surface.

12. The wrench assembly of claim 7, wherein the adapter comprises a plurality of tabs, wherein the wrench comprises a shoulder, and wherein the plurality of tabs are configured to engage the shoulder.

13. The wrench assembly of claim 12, wherein the plurality of tabs are configured to flex relative to the shoulder.

14. The wrench assembly of claim 7, wherein the adapter further comprises a skirt surrounding the spline gear.

15. The wrench assembly of claim 7, wherein the wrench comprises a collar surrounding the longitudinal axis, and wherein the plurality of arms are defined in the collar.

16. An ultrasonic surgical system, comprising:
a surgical instrument, comprising:
a handle comprising a first finger grip;
a body pivotably coupled to the handle, wherein the body comprises:
a second finger grip;
a clamp arm extending from the second finger grip;
a first body surface defined on a first side of the clamp arm; and
a second body surface defined on a second side of the clamp arm; and
a wrench assembly, comprising:
a wrench; and
an adapter operably coupled to the wrench, wherein the adapter comprises:
a first wrench surface configured to interface with the first body surface; and
a second wrench surface configured to interface the second body surface.

17. The ultrasonic surgical system of claim 16, wherein the handle further comprises an ultrasonic blade and a waveguide extending proximally from the ultrasonic blade.

18. The ultrasonic surgical system of claim 16, wherein the wrench is configured to rotate relative to the adapter based on a threshold force applied to the wrench being reached or exceeded.

19. The ultrasonic surgical system of claim 16, wherein the handle defines a cavity configured to removably receive a transducer.

20. The ultrasonic surgical system of claim 16, wherein the wrench comprises an arm and a tooth extending from the arm, wherein the adapter comprises a shaft and a spline gear extending from the shaft, wherein the tooth is configured to engage the spline gear based on rotation of the wrench, and wherein the arm is configured to flex away from the spline gear based on a threshold force being applied to the wrench.

* * * * *